United States Patent [19]

Basset et al.

[11] Patent Number: 5,236,844

[45] Date of Patent: Aug. 17, 1993

[54] ANALYTICAL MARKERS FOR MALIGNANT BREAST CANCER

[75] Inventors: Paul Basset; Jean-Pierre Bellocq, both of Strasbourg; Pierre Chambon, Blaesheim, all of France

[73] Assignees: Institut Natl. de la Sante et de la Recherche Medicale; Centre National de la Rescherche Scientifiquue; Universite Louis Pasteur Strasbourg, France

[21] Appl. No.: 794,393

[22] Filed: Nov. 21, 1991

[30] Foreign Application Priority Data

Nov. 21, 1990 [GB] United Kingdom ............... 9025326

[51] Int. Cl.$^5$ .................... C12N 15/70; C07H 21/04
[52] U.S. Cl. .................................. 435/320.1; 536/23.5
[58] Field of Search .................. 435/6, 320.1; 536/27, 536/23.5; 530/350

[56] References Cited

PUBLICATIONS

Chen et al (1990, Sep.) Oncoqche 5(9) 1391-5.
Davis et al (1987) P.N.A.S. 81, 2194-2198.
Salomon et al., in *Breast Cancer: Cellular and Molecular Biology (eds., Lippman, M. E. and Dickson, R. B.), pp. 363-389 (Kluwer, Boston, (1988).*

*Primary Examiner*—Margaret Moskowitz
*Assistant Examiner*—Lisa Bennett
*Attorney, Agent, or Firm*—Sterne, Kessler, Goldstein & Fox

[57] ABSTRACT

The present invention relates to a gene encoding a new member of the metalloproteinase family which has been found to be specifically associated with invasive breast cancer, and to methods of diagnosis for such cancer comprising detection of the marker or its nucleotide sequence, and to treatment or prophylaxis by inhibiting, altering the activity of or binding the marker, or by interfering with its synthesis.

8 Claims, 18 Drawing Sheets

```
CCGGGGCGG ATG GCT CCG GCC GCC TGG CTC CGC AGC GCG GCC GCG CGC                    48
         Met Ala Pro Ala Ala Trp Leu Arg Ser Ala Ala Ala Arg
          1                   5                  10

GCC CTC CTG CCC CCG ATG CTG CTG CTC CTG CTG CAG CCG CCG CCG CTG                   96
Ala Leu Leu Pro Pro Met Leu Leu Leu Leu Leu Gln Pro Pro Pro Leu
         15                  20                  25

CTG GCC CGG GCT CTG GCT CTG CCG CCG GAC GTC CAC CAC CTC CAT GCC GAG AGG          144
Leu Ala Arg Ala Leu Ala Leu Pro Pro Asp Val His His Leu His Ala Glu Arg
         30                  35                  40                  45

AGG GGG CCA CAG CCC TGG CAT GCA GCC CTG CCC AGT AGC CCG GCA CCT                  192
Arg Gly Pro Gln Pro Trp His Ala Ala Leu Pro Ser Ser Pro Ala Pro
         50                  55                  60

GCC CCT GCC ACG CAG GAA GCC CGG CCT GCC AGC AGC CTC AGG CCT                      240
Ala Pro Ala Thr Gln Glu Ala Arg Pro Ala Ser Ser Leu Arg Pro
         65                  70                  75

CCC CGC TGT GGC GTG GTG CCC GAC CCA TCT GAT GGG CTG AGT GCC CGC AAC              288
Pro Arg Cys Gly Val Val Pro Asp Pro Ser Asp Gly Leu Ser Ala Arg Asn
         80                  85                  90

CGA CAG AAG AGG TTC GTG CTT TCT GGC GGG CGC TGG GAG AAG ACG GAC                  336
Arg Gln Lys Arg Phe Val Leu Ser Gly Gly Arg Trp Glu Lys Thr Asp
         95                 100                 105
```

FIG. 2A

```
CTC ACC TAC AGG ATC CTT CGG TTC CCA TGG CAG TTG GTG CAG GAG CAG      384
Leu Thr Tyr Arg Ile Leu Arg Phe Pro Trp Gln Leu Val Gln Glu Gln
110                 115                 120                 125

GTG CGG CAG ACG ATG GCA GAG GCC CTA AAG GTA TGG AGC GAT GTG ACG      432
Val Arg Gln Thr Met Ala Glu Ala Leu Lys Val Trp Ser Asp Val Thr
        130                 135                 140

CCA CTC ACC TTT GAG ACT GAG GTG CAC GAG GGC CGT GCT GAC ATC ATG ATC  480
Pro Leu Thr Phe Glu Thr Glu Val His Glu Gly Arg Ala Asp Ile Met Ile
    145                 150                 155

GAC TTC GCC AGG TAC TGG CAT GGG TTT GAT GGG CCT CCG TTT CCC AAG ACT  528
Asp Phe Ala Arg Tyr Trp His Gly Phe Asp Gly Pro Pro Phe Pro Lys Thr
160                 165                 170                 185

GGG GGC ATC CTG GCC CAT GCC TTC TTC GAC CTG CCG AAG ACT CAC CGA GAA GGG
Gly Gly Ile Leu Ala His Ala Phe Phe Asp Leu Pro Lys Thr His Arg Glu Gly
175                 180                                 185

GAT GTC CAC TTC GAC TAT GAT GAG ACC TGG ACT ATC GGG GAT GAC CAG        624
Asp Val His Phe Asp Tyr Asp Glu Thr Trp Thr Ile Gly Asp Asp Gln
190                 195                 200                 205

GGC ACA GAC CTG CTG CAG GTG GCA GCC CAT GAA TTT GGC CAC GTG CTG       672
Gly Thr Asp Leu Leu Gln Val Ala Ala His Glu Phe Gly His Val Leu
    210                 215                 220
```

FIG.2B

```
GGG CTG CAG CAC ACA ACA GCA AAG GCC CTG ATG TCC GCC TTC TAC      720
Gly Leu Gln His Thr Thr Ala Lys Ala Leu Met Ser Ala Phe Tyr
            225             230             235

ACC TTT CGC TAC CCA CCA CTG AGT CTC AGC CCA GAT GAC TGC GTT      768
Thr Phe Arg Tyr Pro Pro Leu Ser Leu Ser Pro Asp Asp Cys Val
        240             245             250

CAA CAC CTA TAT GGC CAG CCC TGG CCC ACT GTC ACC TCC AGG ACC CCA  816
Gln His Leu Tyr Gly Gln Pro Trp Pro Thr Val Thr Ser Arg Thr Pro
        255             260             265

GCC CTG GCT GGG ATA GAC ACC AAT GAG ATT GCA CCG CTG            864
Ala Leu Ala Gly Ile Asp Thr Asn Glu Ile Ala Pro Leu
270             275             280             285

GAG CCA GAT GCC CCG GAT GCC TGT GAG GCC TCC TTT GAC GCG GTC      912
Glu Pro Asp Ala Pro Asp Ala Cys Glu Ala Ser Phe Asp Ala Val
            290             295             300

TCC ACC ATC CGA GGC GGA GAG CTC TTC TTC AAA GCG GGC TTT GTG TGG  960
Ser Thr Ile Arg Gly Gly Glu Leu Phe Phe Lys Ala Gly Phe Val Trp
        305             310             315

CGC CTC CGT GGC GGC CAG CTG CAG CCC GGC TAC CCA GCA TTG GCC TCT  1008
Arg Leu Arg Gly Gly Gln Leu Gln Pro Gly Tyr Pro Ala Leu Ala Ser
        320             325             330
```

FIG. 2C

```
CGC CAC TGG CAG GGA CTG CCC AGC CCT GTG GAC GCT GCC TTC GAG GAT         1056
Arg His Trp Gln Gly Leu Pro Ser Pro Val Asp Ala Ala Phe Glu Asp
335                 340                 345

GCC CAG GGC CAC ATT TGG TTC CAA GGT GCT CAG TAC TGG GTG TAC             1104
Ala Gln Gly His Ile Trp Phe Gln Gly Ala Gln Tyr Trp Val Tyr
350                 355                 360             365

GAC GGT GAA AAG CCA GTC CTG GGC CCC GCA CCC CTC ACC GAG CTG GGC         1152
Asp Gly Glu Lys Pro Val Leu Gly Pro Ala Pro Leu Thr Glu Leu Gly
                370                 375                 380

CTG GTG AGG TTC CCG GTC CAT GCT GCC TTG GTC TGG GGT CCC GAG AAG         1200
Leu Val Arg Phe Pro Val His Ala Ala Leu Val Trp Gly Pro Glu Lys
385                 390                 395

AAC AAG ATC TAC TTC CGA GGC AGG GAC TAC TGG CGT TTC CAC CCC             1248
Asn Lys Ile Tyr Phe Arg Gly Arg Asp Tyr Trp Arg Phe His Pro
            400                 405                 410

AGC ACC CGG CGT GTA GAC AGT CCC GTG CCC CGC AGG GCC ACT GAC TGG         1296
Ser Thr Arg Arg Val Asp Ser Pro Val Pro Arg Arg Ala Thr Asp Trp
415                 420                 425

AGA GGG GTG CCC TCT GAG ATC GAC GCT GCC TTC CAG GAT GCT GAT GGC         1344
Arg Gly Val Pro Ser Glu Ile Asp Ala Ala Phe Gln Asp Ala Asp Gly
430                 435                 440                 445
```

FIG. 2D

```
TAT GCC TAC TTC CTG CGC GGC CGC CTC TAC TGG AAG TTT GAC CCT GTG      1392
Tyr Ala Tyr Phe Leu Arg Gly Arg Leu Tyr Trp Lys Phe Asp Pro Val
              450                 455                 460

AAG GTG AAG GCT CTG GAA GGC TTC CCC CGT CTC GTG GGT CCT GAC TTC      1440
Lys Val Lys Ala Leu Glu Gly Phe Pro Arg Leu Val Gly Pro Asp Phe
              465                 470                 475

TTT GGC TGT GCC GAG CCT GCC AAC ACT TTC CTC TGACCATGGC TTGGATGCCC    1493
Phe Gly Cys Ala Glu Pro Ala Asn Thr Phe Leu
              480                 485

TCAGGGGTGC TGACCCCTGC CAGGCCACGA ATATCAGGCT AGAGACCCAT GGCCATCTTT    1553
GTGGCTGTGG GCACCAGGCA TGGGACTGAG CCCATGTCTC CTGCAGGGGG ATGGGGTGGG    1613
GTACAACCAC CATGACAACT GCCGGGAGGG CCACGCAGGT CGTGGTCACC TGCCAGCGAC    1673
TGTCTCAGAC TGGGCAGGA GGCTTTGGCA TGACTTAAGA GGAAGGGCAG TCTTGGACC      1733
CGCTATGCAG GTCCTGGCAA ACCTGGCTGC CCTGTCTCAT CCCTGTCCCT CAGGGTAGCA    1793
CCATGGCAGG ACTGGGGGAA CTGGAGTGTC CTTGCTGTAT CCCTGTTGTG AGTTCCTTC     1853
CAGGGGCTGG CACTGAAGCA AGGGTGCTGG GGCCCCATGG CCTTCAGCCC TGGCTGAGCA    1913
ACTGGGCTGT AGGGCAGGGC CACTTCCTGA GGTCAGGTCT TGGTAGGTGC CTGCATCTGT    1973
```

FIG. 2E

```
CTGCCTTCTG GCTGACAATC CTGGAAATCT GTTCTCCAGA ATCCAGGCCA AAAAGTTCAC    2033
AGTCAAATGG GGAGGGTAT  TCTTCATGCA GGAGACCCCA GGCCCTGGAG GCTGCAACAT    2093
ACCTCAATCC TGTCCCAGGC CGGATCCTCC TGAAGCCCTT TTCGCAGCAC TGCTATCCTC    2153
CAAAGCCATT GTAAATGTGT GTACAGTGTG TATAAACCTT CTTCTTCTTT TTTTTTTTA    2213
AACTGAGGAT TGTCATTAAA CACAGTTGTT TTCTAAAAAA AAA                      2256
```

FIG. 2F

```
STROMELYSIN3    MAPAAWLR----SAAARALLPPMLLLLLQPPPLLAR------ALPPDVHHLHAERRGPQP    50
STROMELYSIN1    MKSLPILLLLCVAVCSAYPLDGAARGEDTSMNLVQKYLENYYDLEKDVKQFV-RRKDSGP  59
STROMELYSIN2    MMHLAFLVLLCLPVCSAYPLSGAAKEEDSNKDLAQQYLEKYYNLEKDVKQF--RRKDSNL  58
COLLAGENASE1    MHSFPPLLLLLFWGVVSHSFPATLETEQEQDVDLVQKYLEKYYNLKNDGRQVE-KRRNSGP  59
                *  *          *                         *     *   *         *

STROMELYSIN3    WHAALPSSP---APAPATQEAPRPASSLRPPRCGVPDPSD GLSARNRQKR FVLSGG--RW   105
STROMELYSIN1    VVKKIREMQKFLGLEVTGKLDSDTLEVMRKPRCGVPDVGH------------FRTFPGIPKW  109
STROMELYSIN2    IVKKIQGMQKFLGLEVTGKLDTDTLEVMRKPRCGVPDVGH------------FSSFPGMPKW  108
COLLAGENASE1    VVEKLKQMQEFFGLKVTGKPDAETLKVMKQPRCGVPDVAQ------------FVLTEGNPRW  109
                    *             ********              ▲            *      *

STROMELYSIN3    EKTDLTYRILRFPWQLVQEQVRQTMAEALKVWSDVTPLTFTEVHEGRADIMIDFARYWHG   165
STROMELYSIN1    RKTHLTYRIVNYTPDLPKDAVDSAVEKALKYWEEVTPLTFSRLYEGEADIMISFAVREHG  169
STROMELYSIN2    RKTHLTYRIVNYTPDLPRDAVDSAIEKALKVWEEVTPLTFSRLYEGEADIMISFAVKEHG  168
COLLAGENASE1    EQTHLTYRIENYTPDLPRADVDHAIEKAFQLWSNVTPLTFTKVSEGQADIMISFVRGDHR  169
                   * *****                   *       *****  *   *****
```

FIG.3A

| | | |
|---|---|---|
| STROMELYSIN3 | DDLPFDGPGGILAHAFFPKTHREGDVHFDYDETVTIGDDQGTDLLQVAAHEFGHVLGLQH | 225 |
| STROMELYSIN1 | DFYPFDGPGNVLAHAYAPGPGINGDAHFDDDEQWT-KDTTGTNLFLVAAHEIGHSLGLFH | 228 |
| STROMELYSIN2 | DFYSFDGPGHSLAHAYPPGPGLYGDIHFDDDEKVT-EDASGTNLFLVAAHELGHSLGLFH | 227 |
| COLLAGENASE1 | DNSPFDGPGGNLAHAFQPGPGIGGDAHFDEHERVT-NNFTEYNLHRVAAHELGHSLGLSH | 228 |
| | * ***** **** * ** *** * ** *** ** *** *  | |
| STROMELYSIN3 | TTAAKALMSAFYTFRYPLS---LSPDDCRGVQHLYGQPWPTVTSRTPALGPQAGIDTNEI | 282 |
| STROMELYSIN1 | SANTEALMYPLYHSLTDLTRFRLSQDDINGIQSLYGPP---PDSPETPLVPTEPV----- | 280 |
| STROMELYSIN2 | SANTEALMYPLYNSFTELAQFRLSQDDVNGIQSLYGPP---PASTEEPLVPTKSV----- | 279 |
| COLLAGENASE1 | STDIGALMYPSYTFSGDV---QLAQDDIDGIQAIYGRS---QNPVQ-------------- | 268 |
| | * ** * ** * * *** **  | |
| STROMELYSIN3 | APLEPDAPPDACEA--SFDAVSTIRGELFFFKAGFVWRLRGGQLQPGYPALASRHWQGLP | 340 |
| STROMELYSIN1 | -PPEPGTPAN-CDPALSFDAVSTLRGEILIFKDRHFWRKSLRKLEPELH-LISSFWPSLP | 337 |
| STROMELYSIN2 | -PSGSEMPAK-CDPALSFDAISTLRGEYLFFKDRYFWRRSHWNPEPEFH-LISAFWPSLP | 336 |
| COLLAGENASE1 | -PIGPQTPKA-CDSKLTFDAITTIRGEVMFFKDRFYMRTNPFYPEVELN-FISVFWPQLP | 325 |
| | * ** *** * ** ** * *** *** *** ** * ** |  |

FIG.3B

```
STROMELYSIN3   SPVDAAFE-DAQGHIWFFQGAQYWVYDGEKPVLG--PAPLTELGLVRFPVH-AALVWGPE   396
STROMELYSIN1   SGVDAAYEVTSKDLVFIFKGNQFWAIRGNEVRAGYPRGIHT-LGFPPTVRKIDAAISDKE   396
STROMELYSIN2   SYLDAAYEVNSRDTVFIFKGNEFWAIRGNEVQAGYPRGIHT-LGFPPTIRKIDAAVSDKE   395
COLLAGENASE1   NGLEAAYEFADRDEVRFFKGNKYWAVQGQNVLHGYPKDIYSSFGFPRTYKHIDAALSEEN   385
                  *   **                              **                 *

STROMELYSIN3   KNKIYFFRGRDYWRFHPSTRRVDSPVPRR-ATDWRGVPSEIDAAFQDADGYAYFLRGRLY   455
STROMELYSIN1   KNKTYFFVEDKYWRFDEKRNSMEPGFPKQIAEDFPGIDSKIDAVFEEF-GFFYYFFTGSSQ  455
STROMELYSIN2   KKKTYFFAADKYWRFDENSQSMEQGFPRLIADDFPGVEPKVDAVLQAF-GFFYYFFSGSSQ  454
COLLAGENASE1   TGKTYFFVANKYWRYDEYKRSMDPGYPKMIAHDFPGIGHKVDAVFMKD-GFFYYFFHGTRQ  444
                * ***         *                              **  **  **  *

STROMELYSIN3   VKFDPVKVKALEGFPRLVGPDFFGCAEPANTFL   488
STROMELYSIN1   LEFDPNAKKVTHT---LKSNSWLNC--------   477
STROMELYSIN2   FEFDPNARMVTHI---LKSNSWLHC--------   476
COLLAGENASE1   YKFDPKTKRILTL---QKANSWFNCRKN-----   469
                ***                *
```

FIG.3C

```
CCCGGGGCGGATGGCACGGGCCGCCTGTCTCCTCCGCGCGATTTCGGGGTGCCTCCTGCT    60
               M  A  R  A  A  C  L  L  R  A  I  S  G  C  L  L  L    17
CCCGCTGCCTCTGCTGCTCCTGTTGCTGCTGCTCCTGCCGTCGCCGCTGATGGCCCGGGC   120
 P  L  P  L  L  L  L  L  L  L  L  P  S  P  L  M  A  R  A           37
CAGGCCACCGGAGAGTCACCGTCATCACCCTGTGAAGAAAGGGCCTCGGCTCCTGCATGC   180
  R  P  P  E  S  H  R  H  H  P  V  K  K  G  P  R  L  L  H  A       57
AGCTCTGCCTAATACCTTGACATCTGTCCCCGCGTCTCATTGGGTCCCTAGTCCTGCCGG   240
   A  L  P  N  T  L  T  S  V  P  A  S  H  W  V  P  S  P  A  G     77
TAGCTCCAGGCCTCTACGATGTGGTGTGCCCGACCTGCCTGATGTACTGAATGCCCGGAA   300
   S  S  R  P  L  R  C  G  V  P  D  L  P  D  V  L  N  A  R  N     97
CCGACAGAAGCGCTTCGTCCTGTCAGGAGGACGCTGGGAGAAGACAGACCTCACCTATAG   360
   R  Q  K  R  F  V  L  S  G  G  R  W  E  K  T  D  L  T  Y  R    117
GATCCTCCGGTTCCCATGGCAGCTTGTAAGGGAGCAAGTCCGGCAGACAGTGGCAGAGGC   420
   I  L  R  F  P  W  Q  L  V  R  E  Q  V  R  Q  T  V  A  E  A    139
CCTCCAGGTATGGAGTGAAGTGACCCCACTCACTTTCACTGAGGTGCACGAGGGACGCGC   480
   L  Q  V  W  S  E  V  T  P  L  T  F  T  E  V  H  E  G  R  A    157
TGACATCATGATCGACTTCGCAAGGTACTGGGATGGTGACAACTTGCCGTTTGACGGGCC   540
   D  I  M  I  D  F  A  R  Y  W  D  G  D  N  L  P  F  D  G  P    177
TGGGGGCATCCTGGCCCATGGCTTCTTCCCTAAGACCCACCGAGAAGGGGATGTCCACTT   600
   G  G  I  L  A  H  G  F  F  P  K  T  H  R  E  G  D  V  H  F    197
TGACTATGATGAAACTTGGACTATTGGGGACAACCAGGGAACTGACCTGCTGCAAGTGGC   660
   D  Y  D  E  T  W  T  I  G  D  N  Q  G  T  D  L  L  Q  V  A    217
GGCTCATGAATTTGGCCATGTTCTGGGGCTACAACACACCACAGCAGCTAAGGCCCTCAT   720
   A  H  E  F  G  H  V  L  G  L  Q  H  T  T  A  A  K  A  L  M    237
GTCCCCTTTCTACACCTTCCGCTACCCTCTGAGCCTTAGCCCAGATGACCGAAGGGGCAT   780
   S  P  F  Y  T  F  R  Y  P  L  S  L  S  P  D  D  R  R  G  I    257
CCAGCACCTCTATGGGCGGCCCCAGATGACCCCCACCTCCCCCGCCCCAACTTTGAGCTC   840
   Q  H  L  Y  G  R  P  Q  M  T  P  T  S  P  A  P  T  L  S  S    277
CCAGGCTGGGACAGATACCAATGAGATTGCACTGCTGGAGCCGGAAACCCCGCCAGATGT   900
   Q  A  G  T  D  T  N  E  I  A  L  L  E  P  E  T  P  P  D  V    297
CTGTGAGACTTCCTTCGACGCGGTTTCCACCATCCGAGGAGAGCTCTTCTTCTTCAAGGC   960
   C  E  T  S  F  D  A  V  S  T  I  R  G  E  L  F  F  F  K  A    317
AGGCTTTGTGTGGAGGCTGCGCAGTGGGCGACTGCAGCCCGGGTATCCTGCTTTGGCCTC  1020
   G  F  V  W  R  L  R  S  G  R  L  Q  P  G  Y  P  A  L  A  S    337
```

FIG.7A

```
TCGGCACTGGCAAGGACTGCCCAGCCCTGTGGATGCAGCTTTTGAGGATGCCCAGGGCCA  1080
  R  H  W  Q  G  L  P  S  P  V  D  A  A  F  E  D  A  Q  G  Q  357
GATTTGGTTCTTCCAAGGTGCTCAGTACTGGGTATATGATGGTGAGAAGCCAGTCCTAGG  1140
  I  W  F  F  Q  G  A  Q  Y  W  V  Y  D  G  E  K  P  V  L  G  377
CCCTGCACCACTCTCCAAGCTGGGCCTGCAAGGGTCCCCAGTTCATGCCGCCTTGGTCTG  1200
  P  A  P  L  S  K  L  G  L  Q  G  S  P  V  H  A  A  L  V  W  397
GGGTCCTGAGAAGAACAAGATCTACTTCTTCCGAGGTGGAGACTATTGGCGTTTCCACCC  1260
  G  P  E  K  N  K  I  Y  F  F  R  G  G  D  Y  W  R  F  H  P  417
CAGAACCCAGCGAGTGGACAATCCCGTGCCCCGGCGCTCCACTGACTGGCGAGGGGTACC  1320
  R  T  Q  R  V  D  N  P  V  P  R  R  S  T  D  W  R  G  V  P  437
TTCTGAGATTGATGCTGCCTTCCAGGATGCTGAGGGCTATGCCTACTTCCTTCGTGGCCA  1380
  S  E  I  D  A  A  F  Q  D  A  E  G  Y  A  Y  F  L  R  G  H  457
TCTCTACTGGAAGTTTGATCCCGTGAAGGTGAAGGTCCTAGAAGGCTTTCCTCGCCCCGT  1440
  L  Y  W  K  F  D  P  V  K  V  K  V  L  E  G  F  P  R  P  V  477
AGGTCCTGACTTCTTTGACTGTGCTGAGCCTGCCAATACTTTCCGCTGACAACACTTTGG  1500
  G  P  D  F  F  D  C  A  E  P  A  N  T  F  R  -         492
ATGCATTCAGGGGTACTGACTCCTGCCAGGGCACTTAGATCATGTAAGAGACCCACAGCC  1560
ATATCTGTGGCTCTGGCTTCAGGCATGGGACAGACAGGGCCTATGTCTCCTCAGGGGAGT  1620
GGGTTGGGGTGCAGCCACTGTTTGTAGGAACGACCATGCTGTCATGTCACCTGCCAACAA  1680
TTGTCTCAGACTAGGCAAAGGCTTTGGTGTTACTTAAAAATAAGGGAGGTTTTGGGCTGG  1740
CAATATTTCAGCTACCAATAATCCACAGTCAGCCTGGTTGCCCAAGGTCTCCTATCTCTG  1800
TCCCTCAATGTAGAACCCCCACACAAACTCAGGAATCACCTGCAATGAGGTTCCTGTTGG  1860
GAGTGGTGTTGGTAATGAGATGCCCAGGGTACCATGCTGCCCCTGCTAAGCAACTGGACC  1920
AGTATCTTTCCTGGTAAGTCAGCTCTGGAGAGATAGTGAACTGATCATATTCTGGCAGGT  1980
GATTCAGACAAGTGCTTCCTGGAACTCAGGCCCCAAGGTACACAGCCAGCCAAGGAGGCA  2040
GCTGCTTCCTCCCAGAGACACGGAACCTCAAAGGCCCCACATACCTCACAGCCTTGCCCC  2100
AGGCCATTTCTTTCTGGGGCCCTCTTCCTAGCACAGGTACCCTCTAAGCCATGTACATGT  2160
GTATACAGTGTATAAAGACTTTTTTAAAAAAACAAAAAACCAAACCCCAAAAAAGCCAAG  2220
ACTGTCATTAAACATGAGTGTTTTCTAAAAAAAAAAAAAAA                     2260
```

FIG. 7B

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2256 base pairs
        ( B ) TYPE: nucleic acid
        ( C ) STRANDEDNESS: both
        ( D ) TOPOLOGY: linear ( i i ) MOLECULE TYPE: DNA ( i x ) FEATURE:
        ( A ) NAME/KEY: CDS
        ( B ) LOCATION: 10..1473

( x i ) SEQUENCE DESCRIPTION: SEQ ID NO:1:

```
CCGGGGCGG ATG GCT CCG GCC GCC TGG CTC CGC AGC GCG GCC GCG CGC        48
          Met Ala Pro Ala Ala Trp Leu Arg Ser Ala Ala Ala Arg
          1               5                   10

GCC CTC CTG CCC CCG ATG CTG CTG CTG CTG CTC CAG CCG CCG CCG CTG        96
Ala Leu Leu Pro Pro Met Leu Leu Leu Leu Leu Gln Pro Pro Pro Leu
15                  20                  25

CTG GCC CGG GCT CTG CCG CCG GAC GTC CAC CAC CTC CAT GCC GAG AGG       144
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Leu | Ala | Arg | Ala | Leu | Pro | Pro | Asp | Val | His | His | Leu | His | Ala | Glu | Arg |     |
| 30  |     |     |     |     | 35  |     |     |     | 40  |     |     |     |     |     | 45  |     |
| AGG | GGG | CCA | CAG | CCC | TGG | CAT | GCA | GCC | CTG | CCC | AGT | AGC | CCG | GCA | CCT | 192 |
| Arg | Gly | Pro | Gln | Pro | Trp | His | Ala | Ala | Leu | Pro | Ser | Ser | Pro | Ala | Pro |     |
|     |     |     |     | 50  |     |     |     |     | 55  |     |     |     |     | 60  |     |     |
| GCC | CCT | GCC | ACG | CAG | GAA | GCC | CCC | CGG | CCT | GCC | AGC | AGC | CTC | AGG | CCT | 240 |
| Ala | Pro | Ala | Thr | Gln | Glu | Ala | Pro | Arg | Pro | Ala | Ser | Ser | Leu | Arg | Pro |     |
|     |     |     |     | 65  |     |     |     | 70  |     |     |     |     | 75  |     |     |     |
| CCC | CGC | TGT | GGC | GTG | CCC | GAC | CCA | TCT | GAT | GGG | CTG | AGT | GCC | CGC | AAC | 288 |
| Pro | Arg | Cys | Gly | Val | Pro | Asp | Pro | Ser | Asp | Gly | Leu | Ser | Ala | Arg | Asn |     |
|     |     |     | 80  |     |     |     |     | 85  |     |     |     |     | 90  |     |     |     |
| CGA | CAG | AAG | AGG | TTC | GTG | CTT | TCT | GGC | GGG | CGC | TGG | GAG | AAG | ACG | GAC | 336 |
| Arg | Gln | Lys | Arg | Phe | Val | Leu | Ser | Gly | Gly | Arg | Trp | Glu | Lys | Thr | Asp |     |
|     |     | 95  |     |     |     |     | 100 |     |     |     |     | 105 |     |     |     |     |
| CTC | ACC | TAC | AGG | ATC | CTT | CGG | TTC | CCA | TGG | CAG | TTG | GTG | CAG | GAG | CAG | 384 |
| Leu | Thr | Tyr | Arg | Ile | Leu | Arg | Phe | Pro | Trp | Gln | Leu | Val | Gln | Glu | Gln |     |
| 110 |     |     |     |     | 115 |     |     |     |     | 120 |     |     |     |     | 125 |     |
| GTG | CGG | CAG | ACG | ATG | GCA | GAG | GCC | CTA | AAG | GTA | TGG | AGC | GAT | GTG | ACG | 432 |
| Val | Arg | Gln | Thr | Met | Ala | Glu | Ala | Leu | Lys | Val | Trp | Ser | Asp | Val | Thr |     |
|     |     |     |     | 130 |     |     |     |     | 135 |     |     |     |     | 140 |     |     |
| CCA | CTC | ACC | TTT | ACT | GAG | GTG | CAC | GAG | GGC | CGT | GCT | GAC | ATC | ATG | ATC | 480 |
| Pro | Leu | Thr | Phe | Thr | Glu | Val | His | Glu | Gly | Arg | Ala | Asp | Ile | Met | Ile |     |
|     |     |     |     | 145 |     |     |     |     | 150 |     |     |     |     | 155 |     |     |
| GAC | TTC | GCC | AGG | TAC | TGG | CAT | GGG | GAC | GAC | CTG | CCG | TTT | GAT | GGG | CCT | 528 |
| Asp | Phe | Ala | Arg | Tyr | Trp | His | Gly | Asp | Asp | Leu | Pro | Phe | Asp | Gly | Pro |     |
|     |     |     | 160 |     |     |     |     | 165 |     |     |     | 170 |     |     |     |     |
| GGG | GGC | ATC | CTG | GCC | CAT | GCC | TTC | TTC | CCC | AAG | ACT | CAC | CGA | GAA | GGG | 576 |
| Gly | Gly | Ile | Leu | Ala | His | Ala | Phe | Phe | Pro | Lys | Thr | His | Arg | Glu | Gly |     |
|     | 175 |     |     |     |     | 180 |     |     |     |     | 185 |     |     |     |     |     |
| GAT | GTC | CAC | TTC | GAC | TAT | GAT | GAG | ACC | TGG | ACT | ATC | GGG | GAT | GAC | CAG | 624 |
| Asp | Val | His | Phe | Asp | Tyr | Asp | Glu | Thr | Trp | Thr | Ile | Gly | Asp | Asp | Gln |     |
| 190 |     |     |     |     | 195 |     |     |     |     | 200 |     |     |     |     | 205 |     |
| GGC | ACA | GAC | CTG | CTG | CAG | GTG | GCA | GCC | CAT | GAA | TTT | GGC | CAC | GTG | CTG | 672 |
| Gly | Thr | Asp | Leu | Leu | Gln | Val | Ala | Ala | His | Glu | Phe | Gly | His | Val | Leu |     |
|     |     |     |     | 210 |     |     |     |     | 215 |     |     |     |     | 220 |     |     |
| GGG | CTG | CAG | CAC | ACA | ACA | GCA | GCC | AAG | GCC | CTG | ATG | TCC | GCC | TTC | TAC | 720 |
| Gly | Leu | Gln | His | Thr | Thr | Ala | Ala | Lys | Ala | Leu | Met | Ser | Ala | Phe | Tyr |     |
|     |     |     | 225 |     |     |     |     | 230 |     |     |     |     | 235 |     |     |     |
| ACC | TTT | CGC | TAC | CCA | CTG | AGT | CTC | AGC | CCA | GAT | GAC | TGC | AGG | GGC | GTT | 768 |
| Thr | Phe | Arg | Tyr | Pro | Leu | Ser | Leu | Ser | Pro | Asp | Asp | Cys | Arg | Gly | Val |     |
|     |     | 240 |     |     |     |     | 245 |     |     |     |     | 250 |     |     |     |     |
| CAA | CAC | CTA | TAT | GGC | CAG | CCC | TGG | CCC | ACT | GTC | ACC | TCC | AGG | ACC | CCA | 816 |
| Gln | His | Leu | Tyr | Gly | Gln | Pro | Trp | Pro | Thr | Val | Thr | Ser | Arg | Thr | Pro |     |
|     | 255 |     |     |     |     | 260 |     |     |     |     | 265 |     |     |     |     |     |
| GCC | CTG | GGC | CCC | CAG | GCT | GGG | ATA | GAC | ACC | AAT | GAG | ATT | GCA | CCG | CTG | 864 |
| Ala | Leu | Gly | Pro | Gln | Ala | Gly | Ile | Asp | Thr | Asn | Glu | Ile | Ala | Pro | Leu |     |
| 270 |     |     |     |     | 275 |     |     |     |     | 280 |     |     |     |     | 285 |     |
| GAG | CCA | GAC | GCC | CCG | CCA | GAT | GCC | TGT | GAG | GCC | TCC | TTT | GAC | GCG | GTC | 912 |
| Glu | Pro | Asp | Ala | Pro | Pro | Asp | Ala | Cys | Glu | Ala | Ser | Phe | Asp | Ala | Val |     |
|     |     |     |     | 290 |     |     |     |     | 295 |     |     |     |     | 300 |     |     |
| TCC | ACC | ATC | CGA | GGC | GAG | CTC | TTT | TTC | TTC | AAA | GCG | GGC | TTT | GTG | TGG | 960 |
| Ser | Thr | Ile | Arg | Gly | Glu | Leu | Phe | Phe | Phe | Lys | Ala | Gly | Phe | Val | Trp |     |
|     |     |     | 305 |     |     |     |     | 310 |     |     |     |     | 315 |     |     |     |
| CGC | CTC | CGT | GGG | GGC | CAG | CTG | CAG | CCC | GGC | TAC | CCA | GCA | TTG | GCC | TCT | 1008 |
| Arg | Leu | Arg | Gly | Gly | Gln | Leu | Gln | Pro | Gly | Tyr | Pro | Ala | Leu | Ala | Ser |     |
|     |     | 320 |     |     |     |     | 325 |     |     |     |     | 330 |     |     |     |     |
| CGC | CAC | TGG | CAG | GGA | CTG | CCC | AGC | CCT | GTG | GAC | GCT | GCC | TTC | GAG | GAT | 1056 |
| Arg | His | Trp | Gln | Gly | Leu | Pro | Ser | Pro | Val | Asp | Ala | Ala | Phe | Glu | Asp |     |
|     | 335 |     |     |     |     | 340 |     |     |     |     | 345 |     |     |     |     |     |
| GCC | CAG | GGC | CAC | ATT | TGG | TTC | TTC | CAA | GGT | GCT | CAG | TAC | TGG | GTG | TAC | 1104 |
| Ala | Gln | Gly | His | Ile | Trp | Phe | Phe | Gln | Gly | Ala | Gln | Tyr | Trp | Val | Tyr |     |
| 350 |     |     |     |     | 355 |     |     |     |     | 360 |     |     |     |     | 365 |     |

```
GAC GGT GAA AAG CCA GTC CTG GGC CCC GCA CCC CTC ACC GAG CTG GGC      1152
Asp Gly Glu Lys Pro Val Leu Gly Pro Ala Pro Leu Thr Glu Leu Gly
            370                 375                 380

CTG GTG AGG TTC CCG GTC CAT GCT GCC TTG GTC TGG GGT CCC GAG AAG      1200
Leu Val Arg Phe Pro Val His Ala Ala Leu Val Trp Gly Pro Glu Lys
                385                 390                 395

AAC AAG ATC TAC TTC TTC CGA GGC AGG GAC TAC TGG CGT TTC CAC CCC      1248
Asn Lys Ile Tyr Phe Phe Arg Gly Arg Asp Tyr Trp Arg Phe His Pro
            400                 405                 410

AGC ACC CGG CGT GTA GAC AGT CCC GTG CCC CGC AGG GCC ACT GAC TGG      1296
Ser Thr Arg Arg Val Asp Ser Pro Val Pro Arg Arg Ala Thr Asp Trp
        415                 420                 425

AGA GGG GTG CCC TCT GAG ATC GAC GCT GCC TTC CAG GAT GCT GAT GGC      1344
Arg Gly Val Pro Ser Glu Ile Asp Ala Ala Phe Gln Asp Ala Asp Gly
430                 435                 440                 445

TAT GCC TAC TTC CTG CGC GGC CGC CTC TAC TGG AAG TTT GAC CCT GTG      1392
Tyr Ala Tyr Phe Leu Arg Gly Arg Leu Tyr Trp Lys Phe Asp Pro Val
                450                 455                 460

AAG GTG AAG GCT CTG GAA GGC TTC CCC CGT CTC GTG GGT CCT GAC TTC      1440
Lys Val Lys Ala Leu Glu Gly Phe Pro Arg Leu Val Gly Pro Asp Phe
            465                 470                 475

TTT GGC TGT GCC GAG CCT GCC AAC ACT TTC CTC TGACCATGGC TTGGATGCCC   1493
Phe Gly Cys Ala Glu Pro Ala Asn Thr Phe Leu
        480                 485

TCAGGGGTGC TGACCCCTGC CAGGCCACGA ATATCAGGCT AGAGACCCAT GGCCATCTTT   1553
GTGGCTGTGG GCACCAGGCA TGGGACTGAG CCCATGTCTC CTGCAGGGGG ATGGGGTGGG   1613
GTACAACCAC CATGACAACT GCCGGGAGGG CCACGCAGGT CGTGGTCACC TGCCAGCGAC   1673
TGTCTCAGAC TGGGCAGGGA GGCTTTGGCA TGACTTAAGA GGAAGGGCAG TCTTGGGACC   1733
CGCTATGCAG GTCCTGGCAA ACCTGGCTGC CCTGTCTCAT CCCTGTCCCT CAGGGTAGCA   1793
CCATGGCAGG ACTGGGGGAA CTGGAGTGTC CTTGCTGTAT CCCTGTTGTG AGGTTCCTTC   1853
CAGGGGCTGG CACTGAAGCA AGGGTGCTGG GGCCCCATGG CCTTCAGCCC TGGCTGAGCA   1913
ACTGGGCTGT AGGGCAGGGC CACTTCCTGA GGTCAGGTCT TGGTAGGTGC CTGCATCTGT   1973
CTGCCTTCTG GCTGACAATC CTGGAAATCT GTTCTCCAGA ATCCAGGCCA AAAAGTTCAC   2033
AGTCAAATGG GGAGGGGTAT TCTTCATGCA GGAGACCCCA GGCCCTGGAG CTGCAACAT    2093
ACCTCAATCC TGTCCCAGGC CGGATCCTCC TGAAGCCCTT TTCGCAGCAC TGCTATCCTC   2153
CAAAGCCATT GTAAATGTGT GTACAGTGTG TATAAACCTT CTTCTTCTTT TTTTTTTTA    2213
AACTGAGGAT TGTCATTAAA CACAGTTGTT TTCTAAAAAA AAA                     2256
```

( 2 ) INFORMATION FOR SEQ ID NO:2:

( i ) SEQUENCE CHARACTERISTICS:
        ( A ) LENGTH: 488 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Pro Ala Ala Trp Leu Arg Ser Ala Ala Ala Arg Ala Leu Leu
 1               5                  10                  15

Pro Pro Met Leu Leu Leu Leu Leu Gln Pro Pro Leu Leu Ala Arg
            20                  25                  30

Ala Leu Pro Pro Asp Val His His Leu His Ala Glu Arg Arg Gly Pro
        35                  40                  45

Gln Pro Trp His Ala Ala Leu Pro Ser Ser Pro Ala Pro Ala Pro Ala
    50                  55                  60
```

| | | | | | | | | | | | | | | |
|---|---|---|---|---|---|---|---|---|---|---|---|---|---|---|
|Thr|Gln|Glu|Ala|Pro|Arg|Pro|Ala|Ser|Ser|Leu|Arg|Pro|Pro|Arg|Cys|
|65| | | | |70| | | |75| | | | |80|
|Gly|Val|Pro|Asp|Pro|Ser|Asp|Gly|Leu|Ser|Ala|Arg|Asn|Arg|Gln|Lys|
| | | | |85| | | |90| | | | |95| |
|Arg|Phe|Val|Leu|Ser|Gly|Gly|Arg|Trp|Glu|Lys|Thr|Asp|Leu|Thr|Tyr|
| | | |100| | | |105| | | |110| | | |
|Arg|Ile|Leu|Arg|Phe|Pro|Trp|Gln|Leu|Val|Gln|Glu|Gln|Val|Arg|Gln|
| | |115| | | |120| | | |125| | | | |
|Thr|Met|Ala|Glu|Ala|Leu|Lys|Val|Trp|Ser|Asp|Val|Thr|Pro|Leu|Thr|
| |130| | | |135| | | |140| | | | | |
|Phe|Thr|Glu|Val|His|Glu|Gly|Arg|Ala|Asp|Ile|Met|Ile|Asp|Phe|Ala|
|145| | | |150| | | |155| | | | |160| | |
|Arg|Tyr|Trp|His|Gly|Asp|Asp|Leu|Pro|Phe|Asp|Gly|Pro|Gly|Gly|Ile|
| | | |165| | | |170| | | |175| | | | |
|Leu|Ala|His|Ala|Phe|Phe|Pro|Lys|Thr|His|Arg|Glu|Gly|Asp|Val|His|
| | |180| | | |185| | | |190| | | | | |
|Phe|Asp|Tyr|Asp|Glu|Thr|Trp|Thr|Ile|Gly|Asp|Asp|Gln|Gly|Thr|Asp|
| |195| | | |200| | | |205| | | | | | |
|Leu|Leu|Gln|Val|Ala|Ala|His|Glu|Phe|Gly|His|Val|Leu|Gly|Leu|Gln|
|210| | | |215| | | |220| | | | | | | |
|His|Thr|Thr|Ala|Ala|Lys|Ala|Leu|Met|Ser|Ala|Phe|Tyr|Thr|Phe|Arg|
|225| | | |230| | | |235| | | | |240| | |
|Tyr|Pro|Leu|Ser|Leu|Ser|Pro|Asp|Asp|Cys|Arg|Gly|Val|Gln|His|Leu|
| | | |245| | | |250| | | |255| | | | |
|Tyr|Gly|Gln|Pro|Trp|Pro|Thr|Val|Thr|Ser|Arg|Thr|Pro|Ala|Leu|Gly|
| | |260| | | |265| | | |270| | | | | |
|Pro|Gln|Ala|Gly|Ile|Asp|Thr|Asn|Glu|Ile|Ala|Pro|Leu|Glu|Pro|Asp|
| |275| | | |280| | | |285| | | | | | |
|Ala|Pro|Pro|Asp|Ala|Cys|Glu|Ala|Ser|Phe|Asp|Ala|Val|Ser|Thr|Ile|
|290| | | |295| | | |300| | | | | | | |
|Arg|Gly|Glu|Leu|Phe|Phe|Phe|Lys|Ala|Gly|Phe|Val|Trp|Arg|Leu|Arg|
|305| | | |310| | | |315| | | | |320| | |
|Gly|Gly|Gln|Leu|Gln|Pro|Gly|Tyr|Pro|Ala|Leu|Ala|Ser|Arg|His|Trp|
| | | |325| | | |330| | | |335| | | | |
|Gln|Gly|Leu|Pro|Ser|Pro|Val|Asp|Ala|Ala|Phe|Glu|Asp|Ala|Gln|Gly|
| | |340| | | |345| | | |350| | | | | |
|His|Ile|Trp|Phe|Phe|Gln|Gly|Ala|Gln|Tyr|Trp|Val|Tyr|Asp|Gly|Glu|
| | |355| | | |360| | | |365| | | | | |
|Lys|Pro|Val|Leu|Gly|Pro|Ala|Pro|Leu|Thr|Glu|Leu|Gly|Leu|Val|Arg|
|370| | | | |375| | | |380| | | | | | |
|Phe|Pro|Val|His|Ala|Ala|Leu|Val|Trp|Gly|Pro|Glu|Lys|Asn|Lys|Ile|
|385| | | |390| | | |395| | | | | |400| |
|Tyr|Phe|Phe|Arg|Gly|Arg|Asp|Tyr|Trp|Arg|Phe|His|Pro|Ser|Thr|Arg|
| | | |405| | | |410| | | |415| | | | |
|Arg|Val|Asp|Ser|Pro|Val|Pro|Arg|Arg|Ala|Thr|Asp|Trp|Arg|Gly|Val|
| | |420| | | |425| | | |430| | | | | |
|Pro|Ser|Glu|Ile|Asp|Ala|Ala|Phe|Gln|Asp|Ala|Asp|Gly|Tyr|Ala|Tyr|
| |435| | | |440| | | |445| | | | | | |
|Phe|Leu|Arg|Gly|Arg|Leu|Tyr|Trp|Lys|Phe|Asp|Pro|Val|Lys|Val|Lys|
|450| | | |455| | | |460| | | | | | | |
|Ala|Leu|Glu|Gly|Phe|Pro|Arg|Leu|Val|Gly|Pro|Asp|Phe|Phe|Gly|Cys|
|465| | | |470| | | |475| | | | | |480| |
|Ala|Glu|Pro|Ala|Asn|Thr|Phe|Leu| | | | | | | | |
| | | |485| | | | | | | | | | | | |

( 2 ) INFORMATION FOR SEQ ID NO:3:

( i ) SEQUENCE CHARACTERISTICS:
        ( A ) LENGTH: 2260 base pairs
        ( B ) TYPE: nucleic acid
        ( C ) STRANDEDNESS: both
        ( D ) TOPOLOGY: linear ( i i ) MOLECULE TYPE: DNA ( i x ) FEATURE:
        ( A ) NAME/KEY: CDS
        ( B ) LOCATION: 11..1486

( x i ) SEQUENCE DESCRIPTION: SEQ ID NO:3:

```
CCCGGGGCGG ATG GCA CGG GCC GCC TGT CTC CTC CGC GCG ATT TCG GGG           49
           Met Ala Arg Ala Ala Cys Leu Leu Arg Ala Ile Ser Gly
             1           5                      10

TGC CTC CTG CTC CCG CTG CCT CTG CTG CTC CTG TTG CTG CTG CTC CTG          97
Cys Leu Leu Leu Pro Leu Pro Leu Leu Leu Leu Leu Leu Leu Leu Leu
         15              20                  25

CCG TCG CCG CTG ATG GCC CGG GCC AGG CCA CCG GAG AGT CAC CGT CAT         145
Pro Ser Pro Leu Met Ala Arg Ala Arg Pro Pro Glu Ser His Arg His
 30              35                  40                  45

CAC CCT GTG AAG AAA GGG CCT CGG CTC CTG CAT GCA GCT CTG CCT AAT         193
His Pro Val Lys Lys Gly Pro Arg Leu Leu His Ala Ala Leu Pro Asn
             50                  55                  60

ACC TTG ACA TCT GTC CCC GCG TCT CAT TGG GTC CCT AGT CCT GCC GGT         241
Thr Leu Thr Ser Val Pro Ala Ser His Trp Val Pro Ser Pro Ala Gly
             65                  70                  75

AGC TCC AGG CCT CTA CGA TGT GGT GTG CCC GAC CTG CCT GAT GTA CTG         289
Ser Ser Arg Pro Leu Arg Cys Gly Val Pro Asp Leu Pro Asp Val Leu
         80                  85                  90

AAT GCC CGG AAC CGA CAG AAG CGC TTC GTC CTG TCA GGA GGA CGC TGG         337
Asn Ala Arg Asn Arg Gln Lys Arg Phe Val Leu Ser Gly Gly Arg Trp
     95                 100                 105

GAG AAG ACA GAC CTC ACC TAT AGG ATC CTC CGG TTC CCA TGG CAG CTT         385
Glu Lys Thr Asp Leu Thr Tyr Arg Ile Leu Arg Phe Pro Trp Gln Leu
110                 115                 120                 125

GTA AGG GAG CAA GTC CGG CAG ACA GTG GCA GAG GCC CTC CAG GTA TGG         433
Val Arg Glu Gln Val Arg Gln Thr Val Ala Glu Ala Leu Gln Val Trp
                130                 135                 140

AGT GAA GTG ACC CCA CTC ACT TTC ACT GAG GTG CAC GAG GGA CGC GCT         481
Ser Glu Val Thr Pro Leu Thr Phe Thr Glu Val His Glu Gly Arg Ala
            145                 150                 155

GAC ATC ATG ATC GAC TTC GCA AGG TAC TGG GAT GGT GAC AAC TTG CCG         529
Asp Ile Met Ile Asp Phe Ala Arg Tyr Trp Asp Gly Asp Asn Leu Pro
        160                 165                 170

TTT GAC GGG CCT GGG GGC ATC CTG GCC CAT GGC TTC TTC CCT AAG ACC         577
Phe Asp Gly Pro Gly Gly Ile Leu Ala His Gly Phe Phe Pro Lys Thr
175                 180                 185

CAC CGA GAA GGG GAT GTC CAC TTT GAC TAT GAT GAA ACT TGG ACT ATT         625
His Arg Glu Gly Asp Val His Phe Asp Tyr Asp Glu Thr Trp Thr Ile
190                 195                 200                 205

GGG GAC AAC CAG GGA ACT GAC CTG CTG CAA GTG GCG GCT CAT GAA TTT         673
Gly Asp Asn Gln Gly Thr Asp Leu Leu Gln Val Ala Ala His Glu Phe
                210                 215                 220

GGC CAT GTT CTG GGG CTA CAA CAC ACC ACA GCA GCT AAG GCC CTC ATG         721
Gly His Val Leu Gly Leu Gln His Thr Thr Ala Ala Lys Ala Leu Met
            225                 230                 235

TCC CCT TTC TAC ACC TTC CGC TAC CCT CTG AGC CTT AGC CCA GAT GAC         769
Ser Pro Phe Tyr Thr Phe Arg Tyr Pro Leu Ser Leu Ser Pro Asp Asp
        240                 245                 250

CGA AGG GGC ATC CAG CAC CTC TAT GGG CGG CCC CAG ATG ACC CCC ACC         817
```

|     |     |     |     |     |     |     |     |     |     |     |     |     |     |     |     |
| --- | --- | --- | --- | --- | --- | --- | --- | --- | --- | --- | --- | --- | --- | --- | --- |
| Arg | Arg | Gly | Ile | Gln | His | Leu | Tyr | Gly | Arg | Pro | Gln | Met | Thr | Pro | Thr |
| 255 |     |     |     |     | 260 |     |     |     |     | 265 |     |     |     |     |     |

| TCC | CCC | GCC | CCA | ACT | TTG | AGC | TCC | CAG | GCT | GGG | ACA | GAT | ACC | AAT | GAG | 865 |
|---|---|---|---|---|---|---|---|---|---|---|---|---|---|---|---|---|
| Ser | Pro | Ala | Pro | Thr | Leu | Ser | Ser | Gln | Ala | Gly | Thr | Asp | Thr | Asn | Glu | |
| 270 | | | | | 275 | | | | | 280 | | | | | 285 | |

| ATT | GCA | CTG | CTG | GAG | CCG | GAA | ACC | CCG | CCA | GAT | GTC | TGT | GAG | ACT | TCC | 913 |
|---|---|---|---|---|---|---|---|---|---|---|---|---|---|---|---|---|
| Ile | Ala | Leu | Leu | Glu | Pro | Glu | Thr | Pro | Pro | Asp | Val | Cys | Glu | Thr | Ser | |
| | | | | 290 | | | | | 295 | | | | | 300 | | |

| TTC | GAC | GCG | GTT | TCC | ACC | ATC | CGA | GGA | GAG | CTC | TTC | TTC | TTC | AAG | GCA | 961 |
|---|---|---|---|---|---|---|---|---|---|---|---|---|---|---|---|---|
| Phe | Asp | Ala | Val | Ser | Thr | Ile | Arg | Gly | Glu | Leu | Phe | Phe | Phe | Lys | Ala | |
| | | | 305 | | | | | 310 | | | | | 315 | | | |

| GGC | TTT | GTG | TGG | AGG | CTG | CGC | AGT | GGG | CGA | CTG | CAG | CCC | GGG | TAT | CCT | 1009 |
|---|---|---|---|---|---|---|---|---|---|---|---|---|---|---|---|---|
| Gly | Phe | Val | Trp | Arg | Leu | Arg | Ser | Gly | Arg | Leu | Gln | Pro | Gly | Tyr | Pro | |
| | | 320 | | | | | 325 | | | | | 330 | | | | |

| GCT | TTG | GCC | TCT | CGG | CAC | TGG | CAA | GGA | CTG | CCC | AGC | CCT | GTG | GAT | GCA | 1057 |
|---|---|---|---|---|---|---|---|---|---|---|---|---|---|---|---|---|
| Ala | Leu | Ala | Ser | Arg | His | Trp | Gln | Gly | Leu | Pro | Ser | Pro | Val | Asp | Ala | |
| 335 | | | | | 340 | | | | | 345 | | | | | | |

| GCT | TTT | GAG | GAT | GCC | CAG | GGC | CAG | ATT | TGG | TTC | TTC | CAA | GGT | GCT | CAG | 1105 |
|---|---|---|---|---|---|---|---|---|---|---|---|---|---|---|---|---|
| Ala | Phe | Glu | Asp | Ala | Gln | Gly | Gln | Ile | Trp | Phe | Phe | Gln | Gly | Ala | Gln | |
| 350 | | | | | 355 | | | | | 360 | | | | | 365 | |

| TAC | TGG | GTA | TAT | GAT | GGT | GAG | AAG | CCA | GTC | CTA | GGC | CCT | GCA | CCA | CTC | 1153 |
|---|---|---|---|---|---|---|---|---|---|---|---|---|---|---|---|---|
| Tyr | Trp | Val | Tyr | Asp | Gly | Glu | Lys | Pro | Val | Leu | Gly | Pro | Ala | Pro | Leu | |
| | | | 370 | | | | | 375 | | | | | 380 | | | |

| TCC | AAG | CTG | GGC | CTG | CAA | GGG | TCC | CCA | GTT | CAT | GCC | GCC | TTG | GTC | TGG | 1201 |
|---|---|---|---|---|---|---|---|---|---|---|---|---|---|---|---|---|
| Ser | Lys | Leu | Gly | Leu | Gln | Gly | Ser | Pro | Val | His | Ala | Ala | Leu | Val | Trp | |
| | | | 385 | | | | | 390 | | | | | 395 | | | |

| GGT | CCT | GAG | AAG | AAC | AAG | ATC | TAC | TTC | TTC | CGA | GGT | GGA | GAC | TAT | TGG | 1249 |
|---|---|---|---|---|---|---|---|---|---|---|---|---|---|---|---|---|
| Gly | Pro | Glu | Lys | Asn | Lys | Ile | Tyr | Phe | Phe | Arg | Gly | Gly | Asp | Tyr | Trp | |
| | | 400 | | | | | 405 | | | | | 410 | | | | |

| CGT | TTC | CAC | CCC | AGA | ACC | CAG | CGA | GTG | GAC | AAT | CCC | GTG | CCC | CGG | CGC | 1297 |
|---|---|---|---|---|---|---|---|---|---|---|---|---|---|---|---|---|
| Arg | Phe | His | Pro | Arg | Thr | Gln | Arg | Val | Asp | Asn | Pro | Val | Pro | Arg | Arg | |
| | 415 | | | | | 420 | | | | | 425 | | | | | |

| TCC | ACT | GAC | TGG | CGA | GGG | GTA | CCT | TCT | GAG | ATT | GAT | GCT | GCC | TTC | CAG | 1345 |
|---|---|---|---|---|---|---|---|---|---|---|---|---|---|---|---|---|
| Ser | Thr | Asp | Trp | Arg | Gly | Val | Pro | Ser | Glu | Ile | Asp | Ala | Ala | Phe | Gln | |
| 430 | | | | | 435 | | | | | 440 | | | | | 445 | |

| GAT | GCT | GAG | GGC | TAT | GCC | TAC | TTC | CTT | CGT | GGC | CAT | CTC | TAC | TGG | AAG | 1393 |
|---|---|---|---|---|---|---|---|---|---|---|---|---|---|---|---|---|
| Asp | Ala | Glu | Gly | Tyr | Ala | Tyr | Phe | Leu | Arg | Gly | His | Leu | Tyr | Trp | Lys | |
| | | | 450 | | | | | 455 | | | | | 460 | | | |

| TTT | GAT | CCC | GTG | AAG | GTG | AAG | GTC | CTA | GAA | GGC | TTT | CCT | CGC | CCC | GTA | 1441 |
|---|---|---|---|---|---|---|---|---|---|---|---|---|---|---|---|---|
| Phe | Asp | Pro | Val | Lys | Val | Lys | Val | Leu | Glu | Gly | Phe | Pro | Arg | Pro | Val | |
| | | | 465 | | | | | 470 | | | | | 475 | | | |

| GGT | CCT | GAC | TTC | TTT | GAC | TGT | GCT | GAG | CCT | GCC | AAT | ACT | TTC | CGC | | 1486 |
|---|---|---|---|---|---|---|---|---|---|---|---|---|---|---|---|---|
| Gly | Pro | Asp | Phe | Phe | Asp | Cys | Ala | Glu | Pro | Ala | Asn | Thr | Phe | Arg | | |
| | | 480 | | | | | 485 | | | | | 490 | | | | |

| | | | | | | |
|---|---|---|---|---|---|---|
| TGACAACACT | TTGGATGCAT | TCAGGGGTAC | TGACTCCTGC | CAGGGCACTT | AGATCATGTA | 1546 |
| AGAGACCCAC | AGCCATATCT | GTGGCTCTGG | CTTCAGGCAT | GGGACAGACA | GGGCCTATGT | 1606 |
| CTCCTCAGGG | GAGTGGGTTG | GGGTGCAGCC | ACTGTTTGTA | GGAACGACCA | TGCTGTCATG | 1666 |
| TCACCTGCCA | ACAATTGTCT | CAGACTAGGC | AAAGGCTTTG | GTGTTACTTA | AAAATAAGGG | 1726 |
| AGGTTTTGGG | CTGGCAATAT | TTCAGCTACC | AATAATCCAC | AGTCAGCCTG | GTTGCCCAAG | 1786 |
| GTCTCCTATC | TCTGTCCCTC | AATGTAGAAC | CCCCACACAA | ACTCAGGAAT | CACCTGCAAT | 1846 |
| GAGGTTCCTG | TTGGGAGTGG | TGTTGGTAAT | GAGATGCCCA | GGGTACCATG | CTGCCCCTGC | 1906 |
| TAAGCAACTG | GACCAGTATC | TTTCCTGGTA | AGTCAGCTCT | GGAGAGATAG | TGAACTGATC | 1966 |
| ATATTCTGGC | AGGTGATTCA | GACAAGTGCT | TCCTGGAACT | CAGGCCCCAA | GGTACACAGC | 2026 |
| CAGCCAAGGA | GGCAGCTGCT | TCCTCCCAGA | GACACGGAAC | CTCAAAGGCC | CCACATACCT | 2086 |
| CACAGCCTTG | CCCCAGGCCA | TTTCTTTCTG | GGGCCCTCTT | CCTAGCACAG | GTACCCTCTA | 2146 |
| AGCCATGTAC | ATGTGTATAC | AGTGTATAAA | GACTTTTTTA | AAAAAACAAA | AAACCAAACC | 2206 |

CCAAAAAAGC CAAGACTGTC ATTAAACATG AGTGTTTCT AAAAAAAAAA AAAA 2260

( 2 ) INFORMATION FOR SEQ ID NO:4:

( i ) SEQUENCE CHARACTERISTICS:
        ( A ) LENGTH: 492 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ala Arg Ala Ala Cys Leu Leu Arg Ala Ile Ser Gly Cys Leu Leu
 1               5                  10                  15

Leu Pro Leu Pro Leu Leu Leu Leu Leu Leu Leu Leu Leu Pro Ser Pro
            20                  25                  30

Leu Met Ala Arg Ala Arg Pro Pro Glu Ser His Arg His His Pro Val
            35                  40                  45

Lys Lys Gly Pro Arg Leu Leu His Ala Ala Leu Pro Asn Thr Leu Thr
    50                  55                  60

Ser Val Pro Ala Ser His Trp Val Pro Ser Pro Ala Gly Ser Ser Arg
65                  70                  75                  80

Pro Leu Arg Cys Gly Val Pro Asp Leu Pro Asp Val Leu Asn Ala Arg
                85                  90                  95

Asn Arg Gln Lys Arg Phe Val Leu Ser Gly Gly Arg Trp Glu Lys Thr
                100                 105                 110

Asp Leu Thr Tyr Arg Ile Leu Arg Phe Pro Trp Gln Leu Val Arg Glu
            115                 120                 125

Gln Val Arg Gln Thr Val Ala Glu Ala Leu Gln Val Trp Ser Glu Val
        130                 135                 140

Thr Pro Leu Thr Phe Thr Glu Val His Glu Gly Arg Ala Asp Ile Met
145                 150                 155                 160

Ile Asp Phe Ala Arg Tyr Trp Asp Gly Asp Asn Leu Pro Phe Asp Gly
                165                 170                 175

Pro Gly Gly Ile Leu Ala His Gly Phe Phe Pro Lys Thr His Arg Glu
                180                 185                 190

Gly Asp Val His Phe Asp Tyr Asp Glu Thr Trp Thr Ile Gly Asp Asn
            195                 200                 205

Gln Gly Thr Asp Leu Leu Gln Val Ala Ala His Glu Phe Gly His Val
        210                 215                 220

Leu Gly Leu Gln His Thr Thr Ala Ala Lys Ala Leu Met Ser Pro Phe
225                 230                 235                 240

Tyr Thr Phe Arg Tyr Pro Leu Ser Leu Ser Pro Asp Asp Arg Arg Gly
                245                 250                 255

Ile Gln His Leu Tyr Gly Arg Pro Gln Met Thr Pro Thr Ser Pro Ala
            260                 265                 270

Pro Thr Leu Ser Ser Gln Ala Gly Thr Asp Thr Asn Glu Ile Ala Leu
        275                 280                 285

Leu Glu Pro Glu Thr Pro Pro Asp Val Cys Glu Thr Ser Phe Asp Ala
    290                 295                 300

Val Ser Thr Ile Arg Gly Glu Leu Phe Phe Phe Lys Ala Gly Phe Val
305                 310                 315                 320

Trp Arg Leu Arg Ser Gly Arg Leu Gln Pro Gly Tyr Pro Ala Leu Ala
                325                 330                 335

Ser Arg His Trp Gln Gly Leu Pro Ser Pro Val Asp Ala Ala Phe Glu
            340                 345                 350

Asp Ala Gln Gly Gln Ile Trp Phe Phe Gln Gly Ala Gln Tyr Trp Val
```

```
                         355                          360                          365
Tyr Asp Gly Glu Lys Pro Val Leu Gly Pro Ala Pro Leu Ser Lys Leu
    370                     375             380

Gly Leu Gln Gly Ser Pro Val His Ala Ala Leu Val Trp Gly Pro Glu
385                 390             395                         400

Lys Asn Lys Ile Tyr Phe Phe Arg Gly Gly Asp Tyr Trp Arg Phe His
                405                 410                     415

Pro Arg Thr Gln Arg Val Asp Asn Pro Val Pro Arg Arg Ser Thr Asp
            420                 425                     430

Trp Arg Gly Val Pro Ser Glu Ile Asp Ala Ala Phe Gln Asp Ala Glu
        435             440                     445

Gly Tyr Ala Tyr Phe Leu Arg Gly His Leu Tyr Trp Lys Phe Asp Pro
    450                 455                 460

Val Lys Val Lys Val Leu Glu Gly Phe Pro Arg Pro Val Gly Pro Asp
465                 470                 475                     480

Phe Phe Asp Cys Ala Glu Pro Ala Asn Thr Phe Arg
                485                 490
```

ANALYTICAL MARKERS FOR MALIGNANT BREAST CANCER

FIELD OF THE INVENTION

The present invention relates to tumor-associated enzyme markers.

Utilizing DNA sequences encoding stromelysin-3, and antibodies capable of binding to stromelysin-3, the present invention provides methods for diagnosing cancer, specifically malignant breast cancer.

BACKGROUND OF THE INVENTION

The number of deaths around the world from cancer each year continues to be of major concern, with only a few treatments being available for specific types of cancer, and these having no absolute guarantee of success. Most treatments rely on a general "shotgun" approach, killing off rapidly growing cells in the hope that rapidly growing cancerous cells will succumb, either to the treatment, or at least be reduced in numbers to allow the body's system to eliminate the remainder.

The search for cures has been hampered by the discovery that different forms of cancer require different treatments. Given that virtually any part of the body can be affected by cancer, the task becomes enormous.

Nevertheless, despite their differences, cancers also share a number of similarities. Prime amongst these is the growth of undifferentiated tissue. However, even this is not 100% accurate, in that certain cancerous cells do exhibit a degree of differentiation, and this is shown in the sex cancers, such as those of breast and testicle, where tumors may be positive or negative for hormone receptors. Treatment of these tumors depends on the hormone state, and may be as simple as administration of the relevant hormone antagonist, such as tamoxifen.

Another factor which most cancers share is that, in order to be fatal, they must metastasize. Until such time as metastasis occurs, a tumor, although it may be malignant, is confined to one area of the body. This may cause discomfort and/or pain, or even lead to more serious symptoms, but if it can be located, it may be surgically removed and, if done with adequate care, cause no further problems.

However, once metastasis sets in, surgical resection may remove the parent tumor, but cancerous cells have invaded the body, and only chemotherapy, or some particular form of targeting therapy, stands any chance of success.

Thus, the ability to invade locally and to metastasize in organs distant from the primary tumor (tumor progression) is the lethal event in the course of most cancers. Alteration/degradation of the extracellular matrix (ECM) surrounding the primary tumor, and modifications of the tumor cell adhesive properties, are known to be crucial for dissociation of the metastatic cells from the primary tumor cells (Liotta, *Cancer Res.* 46:1–7 (1986); Hart et al., *Biochim. Biophys. Acta* 989:65–84 (1989)).

Tumor angiogenesis is essential for both primary tumor expansion and metastatic tumor spread, and angiogenesis itself requires ECM degradation (Blood et al., *Biochim. Biophys. Acta* 1032:89–118 (1990)). Thus, malignancy is a systemic disease in which interactions between the neoplastic cells and their environment play a crucial role during evolution of the pathological process (Fidler, I. J., *Cancer Metastasis Rev.* 5:29–49 (1986)).

Identifying the alterations in gene expression which are associated with malignant tumors, including those involved in tumor progression, is clearly a prerequisite not only for a full understanding of cancer, but also to develop new rational therapies against cancer. Mutations and/or abnormal control of expression of two groups of cellular genes (the proto-oncogenes and the tumor suppressor genes) have been shown to lead in a multistep process to the loss of normal growth control and to the acquisition of the transformed cell phenotype (Weinberg, R. A., *Cancer Res.* 49:3713–3721 (1989)). However, the molecular mechanisms which lead to tumor progression are much less clear (Nowell, P. C., *Cancer Res.* 46:2203–2207 (1986); Fidler, I. J., *Cytometry* 10:673–680 (1989)).

Thus, a further problem arises, in that the genes characteristic of cancerous cells are very often host genes being abnormally expressed. It is quite often the case that a particular protein marker for a given cancer is over-expressed in that cancer, but is also expressed elsewhere throughout the body, albeit at reduced levels.

Some of the proteins associated with cancers are enzymes which break down the extracellular matrix, which is important for maintaining cells in their proper relationship to each other. One such class is the metalloproteinases (MMPs) (Matrisian, L. M., *Trends Genet.* 6:121–125 (1990)), so called because they bind zinc. However, none has been found to be diagnostic, of cancer, or any particular tumors, although the presence of some may be indicative.

MMPs are involved in a number of physiological and pathological processes in which ECM remodelling and cell migration are implicated, e.g. morphogenesis and embryonic development, rheumatoid arthritis, and tumor invasion and metastasis. MMP inhibitors are known to be able to block tumor invasion and angiogenesis, which are crucial for tumor progression, in experimental models.

All members of the matrix metalloproteinase family are proteinases which degrade at least one component of ECM, are secreted in a latent form and require activation, such as proteolysis (e.g. by plasmin) to become active. Interstitial collagenases specifically attack connective tissue collagens (I to III), whereas type IV collagenases (72 kD and 92 kD) degrade collagens present in the basement membrane and fibronectin. Stromelysins (transins)-1 and -2, and also pump-1, have a much broader substrate specificity, degrading proteoglycans, laminin, fibronectin, and collagens (III to V).

In man, most of the malignant tumors are carcinomas, and among non-smokers, breast cancer is the leading cause of mortality by cancer in woman (Willett, W., *Nature* 338:389–394 (1989)). The expression of several oncogenes has been reported to be altered in malignant breast cells and tumors, but no particular pattern of oncogene/suppressor gene expression can be consistently associated with breast cancer (Gullick, W. J., *Prog. Growth Factor Res.* 2:1–13 (1990)).

However, the neoplastic cells of breast tumors are often embedded in an adipose and mesenchymal stroma, which may also be important in control of their proliferation and in their ability to metastasize. Indeed, it is known that stroma cells can modulate, both positively and negatively, the growth of normal mammary epithelium (Salomon et al., in *Breast Cancer: Cellular and Molecular Biology* (eds., Lippman, M. E. and Dickson, R. B.), pp. 363-389 (Kluwer, Boston, (1988)), and that interactions between the epithelial and stromal components can influence epithelial carcinogenesis in the mammary gland (DeOme et al., *Cancer Res.* 38:2103-2111 (1978)).

The existence of "activated" (Tremblay, *G. Exp. Mol. Pathol.* 31:248-260 (1979)) and/or abnormal (Grey et al., *Proc. Nat. Acad. Sci. USA* 86:2438-2442 (1989)) fibroblasts in malignant breast tumors has been postulated, and it has been proposed that breast cancer could represent a partial escape from dependence on a stromal requirement or an abnormally strong response to a stromal component.

Owing to the nature of cancerous tissue, it is usually relatively easy to set up a continuous culture, or cell line, of a given cancer, a process which makes it easy to study the effects of a given treatment regimen. A significant drawback to such systems lies in their very nature—while the test treatment will establish whether it can act directly against the cells, it is by no means certain what effect the treatment will have in vivo, and biochemical analysis of such lines is inevitably in the absence of the tissue normally surrounding the tumor in vivo.

SUMMARY OF THE INVENTION

It is an object of the invention to identify genes whose expression is increased in breast carcinomas, whereby breast carcinomas are considered as malignant epithelial cells interacting with their surrouding stroma.

We have now found that a previously uncharacterized protein is diagnostic of certain invasive cancers, especially breast carcinomas, head and neck squamous cell carcinomas and skin (squamous and basal cell types) carcinomas. The protein apparently belongs to the group of metalloproteinases, and is referred to as stromelysin-3 herein.

RNA isolated from C1 breast carcinoma and fibroadenoma cells was probed using four independently isolated cDNA probes as described in example 1.

FIG. 2. Nucleotide sequence of stromelysin-3 cDNA.

The nucleotide sequence of the cDNA and the deduced amino acid sequence of stromelysin-3 is presented. Starting from the 5' end, the underlying nucleotide sequences correspond to: the punitive signal peptide; the PRCGBPD sequence characteristic of prometalloproteinase, the conserved histidine residues of the zinc binding domain and the poly(A+) signal sequence.

Figure 3D:
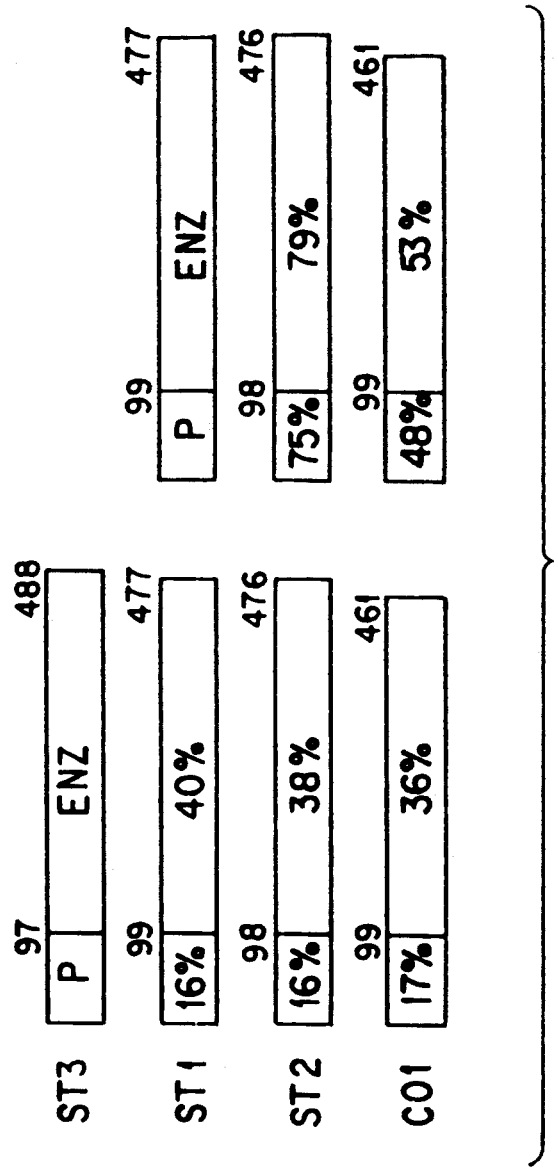

FIG. 3. Comparison of Metalloproteinase Sequences.

Amino acid sequences are aligned and compared for stromelysin-3, stromelysin-2, stromelysin-1 and collagenase-1, all putative metalloproteinase, as described in example 3.

FIG. 4. Northern Blot Analysis of Human Metalloproteinase

Total RNA was prepared from four oestrogen receptor negative breast carcinomas (C1, grade II; C2, C3 and C4, grade III), six oestrogen receptor positive breast carcinomas (C5, C8 and C9, grade II; C6 and C7, grade III; Cio, grade I) and four breast fibroadenomas (F2-F5).

The RNA was probed with (a) stromelysin-3 RNA, (b) type 1 collagenase RNA (COI) (c) 92 kd type 4 collagenase RNA (COIV 92k) (d) 72 kd type 4 collagenase RNA (COIV 72k) (e) stromelysin-1 and 2 RNA (ST1/2) and pump-1 RNA (PUI), as described in example 4.

FIG. 5. Northern Blot Analysis of Stromelysin-3 RNA From Various Cell Lines and Tissues.

(a) Three normal and five metastatic auxiliary lymph nodes from patients with breast cancer; (b) F o u r oestrogen receptive negative (BT-20, MDA-231, SK-BR-3, HBL-100) and four oestrogen receptor positive (T-47D, BT-474, ZR-75-1, MCF-7) breast carcinoma lines; (c) Ten normal human tissues; and (d) HFL-1 Human Foetal Deployed Fibroblasts (ATCC CCL 153) cultured in serum free medium (1 and 2), in the absence (1) or presence (2) of tPA are cultured in serum free media supplemented with 20 mg/ml insulin (3-6), in the absent (3) or presence (4) of PDGF, (5) of EGF, or (6) of bFGF, were probed with stromelysin-3 sequences, as described in example 5.

FIG. 6. Localization of Stromelysin-3 RNA Transcripts in Sections of Breast Carcinoma and Embryolimbuds.

Bright field micrographics of tissue sections (X 100) stained with hematoxylin (A,C,E,G,I and K); and dark field images of the same sections (still stained with hematoxylin) after in situ hybridization with anti-sense stromelysin-3 cRNA (B,D,F,H,J and L) as described in example 6.

FIG. 7. cDNA Sequence of Mouse ST3 cDNA.

cDNA sequence of mouse ST3 gene and comparison with human ST3 cDNA sequences.

DETAILED DESCRIPTION OF THE INVENTION

In a first aspect, the present invention provides a process for the diagnosis of invasive cancer, especially breast, head and neck, and skin carcinomas, comprising the detection of either stromelysin-3, or a nucleotide sequence encoding stromelysin-3.

In an alternative aspect, the present invention provides the use of an agent to interfer with the synthesis or activity of stromelysin-3 in the treatment or prophylaxis of invasive cancer, especially breast, head and neck, and skin carcinomas.

It will be appreciated that metastatic tumors are invasive, but that invasive tumors are not necessarily metastatic (for example basal cell skin carcinomas).

As expression of the stromelysin-3 gene is specific to regions of ECM degradation and apparently encodes a metalloproteinase, it is assumed that its ECM degrading activity is crucial to tumor progression into metastasis. Expression of stromelysin-3 by the stromal cells is likely to break down an important part of the ECM, thereby allowing cancerous cells to migrate away from the parent tumor.

Accordingly, any agent which can affect the activity of stromelysin-3 will have an effect on metastasis. Such agents will suitably be those which either prevent synthesis of the protein, prevent maturation of the protein, or alter the activity of the enzyme, either by blocking or by altering its activity.

Expression of the stromelysin-3 gene was found to be, in the first instance, diagnostic of breast cancer in the metastatic phase. In fact, this result was achieved by the detection of mRNA in a variety of resected tumors. Breast cancer was chosen, as this is responsible for the highest death rate, by cancer, in the non-smoking female population.

Stromelysin-3 is a novel protein almost certainly belonging to the MMP family, and is associated with invasive breast carcinomas, irrespective of their hormonal status.

The members of the MMP family require an activation step, which may be associated with removal of the pre- and pro-sequences, to become active. The amino acid sequence of pro- and mature stromelysin-3 is notably different from those of the previously characterized MMPs, and may exhibit distinct properties regarding maturation, activation and specificity for ECM components.

The stromelysin-3 gene is expressed by all primary invasive breast carcinomas, by some of their metastases, and in tissues in which extensive ECM remodelling is known to occur (uterus, placenta and limb bud) analyzed for such expression, but not in breast fibroadenomas and normal adult tissues, suggesting that the stromelysin-3 gene product plays an important role in breast cancer progression. Also in agreement with this concept, the stromelysin-3 gene is not expressed in most in situ breast carcinomas, with the exception of in situ carcinomas of the comedo type, which are usually considered as preinvasive lesions and are often associated with microinvasion. Thus the presence of stromelysin-3 RNA transcripts in other than the low concentrations found elsewhere in the body, other than uterus or placenta, is diagnostic of a metastatic cancer or of a cancer with a high risk of becoming invasive.

Stromelysin-3 may be involved in the lytic processes which are likely to be associated with invasive tumor growth. Alternatively, it is possible that stromelysin-3 could also play a role in the formation of desmoplasia, which is associated with most invasive breast cancer lesions, and may represent a host reaction to prevent further malignant cell spread (Ahmed, A., *Pathol. Annu.* 25(Pt2):237–286 (1990)). In such an instance, enhancement of stromelysin-3 activity would be advantageous.

Further, the restricted expression of the stromelysin-3 gene in stromal fibroblasts immediately surrounding the neoplastic cell islands is strikingly in contrast to collagenase IV, another metalloproteinase known to be associated with the malignant conversion of some tumorigenic cells, and cathepsin D, a lysosomal aspartyl protease whose expression is increased in breast carcinomas, both of which are expressed, not in the fibroblasts, but in the neoplastic epithelial cells of breast cancers (Monteagudo et al., *Am. J. Pathol.* 136:585–592 (1990); Garcia et al., *Steroid Biochem.* 27:439–445 (1987)).

To identify the novel breast cancer marker, a cDNA library was constructed, and substracted with poly (A+) RNA from a fibroadenoma source. By this process, the cDNA library was enriched for sequences characteristic of metastatic cancers.

A number of clones was grown up and screened using probes derived from poly(A+) RNA from metastatic tumors and from fibroadenomas. Those clones which bound more greatly to the probes derived from metastatic cancer poly(A+) RNA were then grown up further.

Of the clones generated in this manner, one was found to be differentially expressed to the extent that high rates of expression were only found in malignant breast and pharyngeal cancers, head, neck, and skin (squamous and basal cell type) carcinomas, as well as in the uterus and placenta, in all of which there is a breaking down of the ECM, which, when associated with cancer, allows cancerous cells to spread around the body (metastasis).

In the case of the uterus and the placenta, breakdown of the ECM occurs naturally, whilst the same event elsewhere is likely to be characteristic of tumor growth.

It is also interesting to note that expression of the stromelysin-3 gene was found in interdigital differentiation during limb budding in the foetus, which is associated with breakdown of the ECM.

Characterization of the cDNA sequence illustrated that there was an open reading frame. Comparison of the encoded protein sequence with a known library established that the protein belonged to a family known to break down the ECM. Although the sequence of stromelysin-3 bears less similarity to the other members of its family than any of the other members bear to each other, it does, nevertheless, present a number of characteristic regions which serve to identify the nature of the enzyme. Accordingly, the protein has been named stromelysin-3, although it may be a collagenase, or may break down a different constituent of the ECM altogether.

Construction of nucleotide probes to establish the occurrence of stromelysin-3 mRNA revealed a tissue distribution as described above, and also enabled photomicrographs to exactly locate the areas of expression of the stromelysin-3 gene by labelling.

An analysis of the photomicrographs generated by this method showed, somewhat suprisingly, that the stromelysin-3 gene was not expressed in the cancerous cells itself, but in the surrounding stroma. In addition, the stroma did not exhibit any evidence of stromelysin-3 mRNA when the basement membrane of the tumor was still intact (see FIG. 6). The stromelysin-3 gene is expressed by all primary invasive breast carcinomas, by some of their metastases nodes, and in tissues in which extensive ECM remodelling is known to occur (uterus, placenta and limb bud) analyzed for such expression, but not in breast fibroadenomas and normal adult tissues, suggesting that the stromelysin-3 gene product plays an important role in breast cancer progression. Also in agreement with this concept, the stromelysin-3 gene is not expressed in most in situ breast carcinomas, with the exception of in situ carcinomas of the comedo type, which are usually considered as preinvasive lesions and are often associated with microinvasion. Stromelysin-3 always occurs in the stroma of metastatic cancers, and does not occur in the stroma of in situ primary tumors (tumors still having a basement membrane and which are non-invasive). Thus the presence of stromelysin-3 RNA transcripts in other than the low concentrations found elsewhere in the body, other than uterus or placenta, is diagnostic of a metastatic cancer or of a cancer with a high risk of becoming invasive.

Furthermore, expression of the stromelysin-3 gene was not detected in any ER-positive or negative breast cancer cell lines, even though some of them are known to secrete and possess receptors for EGF/TGF-α and FGF (factors which are implicated in expression of the stromelysin-3 gene).

Accordingly, standard detection techniques applied to stromelysin-3, its precursors or its coding nucleotide sequences may be used to diagnose a metastatic cancer, or to confirm that a primary tumor has not yet reached the fatal metastatic phase.

Such techniques may include detection with nucleotide probes, such as in the manner described above, or may comprise detection of the stromelysin-3 protein by, for example, antibodies or their equivalent.

The nucleotide probes may be any that will hybridize more strongly to the sequence shown in the accompanying FIG. 2 than to other naturally occurring sequences. Types of probe include cDNA, riboprobes, synthetic oligonucleotides and genomic probes. The type of probe used will generally be dictated by the particular situation, such as riboprobes for in situ hybridization, and cDNA for Northern blotting, for example. The most preferred probes are those which correspond to the negative strand of the cDNA of FIG. 2. It is also possible to provide probes which recognize introns located within the stromelysin-3 gene, but this is not necessarily as reliable as detecting RNA transcripts.

Detection of the stromelysin-3 encoding gene, per se, will generally serve no purpose in diagnosis, but other forms of assay to detect transcripts and other expression products will generally be useful. The probes may be as short as is required to differentially recognize stromelysin-3 mRNA transcripts, and may be as short as, for example, 15 bases.

The form of labelling of the probes may be any that is appropriate, such as the use of radioisotopes, for example, $^{32}P$ and $^{35}S$. Labelling with radioisotopes may be achieved, whether the probe is synthesized chemically or biologically, by the use of suitably labelled bases. Other forms of labelling may include enzyme or antibody labelling such as is characteristic of ELISA, but detection of mRNA transcripts by labelled probes will generally be by way of X-radiography.

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabelled cDNA or RNA is then hybridized to the preparation, washed and analyzed by autoradiography.

In situ hybridization visualization may also be employed (Example 6), wherein a [$^{35}S$]-labelled antisense cRNA probe is hybridized with a thin section of a biopsy sample, washed, cleaved with RNase and exposed to a sensitive emulsion for autoradiography. The samples may be stained with haematoxylin to demonstrate the histological composition of the sample, and dark field imaging with a suitable light filter shows up the developed emulsion.

Immunohistochemistry may be used to detect expression of stromelysin-3 in a biopsy sample. A suitable antibody is brought into contact with, for example, a thin layer of cells, washed, and then contacted with a second, labelled antibody. Labelling may be by enzyme, such as peroxidase, avidin or by radiolabelling. Chromogenic labels are generally preferable, as they can be detected under a microscope.

More generally preferred is to detect the protein by immunoassay, for example by ELISA or RIA, which can be extremely rapid. Thus, it is generally preferred to use antibodies, or antibody equivalents, to detect stromelysin-3, but use of a suitably labelled stromelysin-3 substrate may also be advantageous.

It may not be necessary to label the substrate, provided that the product of the enzymatic process is detectable and characteristic in its own right (such as hydrogen peroxide for example). However, if it is necessary to label the substrate, then this may also comprise enzyme labelling, labelling with radioisotopes, antibody labelling, fluorescent marker labelling or any other suitable form which will be readily apparent to those skilled in the art.

Most preferred for detecting stromelysin-3 expression is the use of antibodies. Antibodies may be prepared as described below, and used in any suitable manner to detect expression of stromelysin-3.

Antibody-based techniques include ELISA (enzyme linked immunosorbent assay) and RIA (radioimmunoassay). Any conventional procedures may be employed for such immunoassays. The procedures may suitably be conducted such that: a stromelysin-3 standard is labelled with a radioisotope such as $^{125}I$ or $^{35}S$, or an assayable enzyme, such as horseradish peroxidase or alkaline phosphatase and, together with the unlabelled sample, is brought into contact with the corresponding antibody, whereon a second antibody is used to bind the first and radioactivity or the immobilized enzyme assayed (competitive assay); alternatively, stromelysin-3 in the sample is allowed to react with the corresponding immobilized antibody, radioisotope- or enzyme-labelled anti-stromelysin-3 antibody is allowed to react with the system and radioactivity or the enzyme assayed (ELISA-sandwich assay). Other conventional methods may also be employed as suitable.

The above techniques may be conducted essentially as a "one-step" or "two-step" assay. The "one-step" assay involves contacting antigen with immobilized antibody and, without washing, contacting the mixture with labeled antibody. The "two-step" assay involves washing before contacting the mixture with labeled antibody. Other conventional methods may also be employed as suitable.

Enzymatic and radio-labelling of stromelysin-3 and-/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labelling are not particularly limited, but may be selected from the members of the oxidase group, for example. These catalyze the production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labelled antibody with the substrate under controlled conditions well-known in the art.

Other techniques may be used to detect stromelysin-3 according to preference. One such is Western blotting (Towbin et al., *Proc. Nat. Acad. Sci.* 76:4350 (1979)), wherein a suitably treated sample is run on an SDS PAGE gel before being transferred to a solid support, such as a nitrocellulose filter. Anti-stromelysin-3 antibodies (unlabelled) are then brought into contact with the support and assayed by a secondary immunological reagent, such as labelled protein A or anti-immunoglobulin (suitable labels including $^{125}$I, horseradish peroxidase and alkaline phosphatase).

Samples for diagnostic purposes may be obtained from any relevant site. A sample obtained direct from the tumor, such as the stroma or cytosol, may be ideal, but it may also be appropriate to obtain the sample from blood, for example. However, if the sample is derived from blood, highly sensitive assays may be required, as the amount of stromelysin-3 would then be diluted through the bloodstream. Such diagnosis may be of particular importance in monitoring progress of a patient, such as after surgery to remove a tumor. If a reference reading is taken after the operation, then another taken at regular intervals, any rise could be indicative of a relapse, or possibly a metastasis. The taking of such readings may need to take into account activity in the uterus, for example.

Anti-stromelysin-3 antibodies may also be used for imaging purposes. Besides enzymes, other suitable labels include radioisotopes, iodine ($^{125}$I, $^{121}$I), carbon ($^{14}$C), salphee ($^{35}$S), tritium ($^{3}$H), indium ($^{112}$In), and technetium ($^{99m}$Tc), fluorescent labels, such as fluorescein and rhodamine, and biotin.

However, for in vivo imaging purposes, the position becomes more restrictive, as antibodies are not detectable, as such, from outside the body, and so must be labelled, or otherwise modified, to permit detection.

Markers for this purpose may be any that do not substantially interfere with the antibody binding, but which allow external detection. Suitable markers may include those that may be detected by X-radiography, NMR or ESR. For X-radiographic techniques, suitable markers include any radioisotope that emits detectable radiation but that is not overtly harmful to the patient, such as barium or caesium, for example. Suitable markers for NMR and ESR generally include those with a detectable characteristic spin, such as deuterium, which may be incorporated into the antibody by suitable labelling of nutrients for the relevant hybridoma, for example.

In the case of in vivo imaging methods, an antibody or antibody fragment which has been labelled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the subject (such as a human) to be examined.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99m. the labelled antibody or antibody fragment will then preferentially accumulate at the location of cells which contain stromelysin-3. The labelled antibody or antibody fragment can then be detected using known techniques.

For a general discussion of this technological area, see S. W. Burchiel et al., "Immunopharmacokinetics of Radiolabelled Antibodies and Their Fragments" (Chapter 13 in *Tumor Imaging: The Radiochemical Detection of Cancer*, eds., S. W. Burchiel and B. A. Rhodes, Masson Publishing Inc. (1982)).

The antibodies may be raised against either a peptide of stromelysin-3 or the whole molecule. Such a peptide may be presented together with a carrier protein, such as an albumin, to an animal system or, if it is long enough, say 25 amino acid residues, without a carrier. Human antibodies are unlikely to be able to recognize stromelysin-3, as this protein will represent a self protein.

As used herein, the term "peptide" means any molecule comprising 2 or more amino acids linked via a peptide bond. As such, the term includes oligopeptides, polypeptides and proteins.

Polyclonal antibodies generated by the above technique may be used direct, or suitable antibody producing cells may be isolated from the animal and used to form a hybridoma by known means (Kohler and Milstein, *Nature* 256:795 et seq. (1975)). Selection of an appropriate hybridoma will also be apparent to those skilled in the art, and the resulting antibody may be used in a suitable assay to identify stromelysin-3.

Antibodies, or their equivalents, may also be used in accordance with the present invention for the treatment or prophylaxis of metastatic cancers. Administration of a suitable dose of the antibody may serve to block production, or to block the effective activity of stromelysin-3, and this may provide a crucial time window in which to treat the malignant growth.

Prophylaxis may be appropriate even at very early stages of the disease, as it is not known what actually leads to metastasis in any given case. Thus, administration of the antibodies, their equivalents, or factors, such as TIMPs (naturally occurring compounds which regulate the MMPs-tissue inhibitors of metalloproteinases), which interfere with stromelysin-3 activity, may be effected as soon as cancer is diagnosed, and treatment continued for as long as is necessary, preferably until the threat of the disease has been removed.

A preferred form of treatment is to employ the so-called magic bullet technique, where a suitable toxin is attached to the antibodies which then target the area of the tumor. Such toxins are well known in the art, and may comprise toxic radioisotopes, heavy metals, enzymes and complement activators, as well as such natural toxins as ricin which are capable of acting at the level of only one or two molecules per cell. It may also be possible to use such a technique to deliver localized doses of hormone antagonists or any other suitable physiologically active compounds, which may be used, for example, to treat cancers.

It will be appreciated that antibodies for use in accordance with the present invention, whether for diagnostic or therapeutic applications, may be monoclonal or polyclonal as appropriate. Antibody equivalents of these may comprise: the Fab' fragments of the antibodies, such as Fab, Fab', F(ab')$_2$ and Fv; idiotopes; or the results of allotope grafting (where the recognition region of an animal antibody is grafted into the appropriate region of a human antibody to avoid an immune response in the patient), for example. Other suitable modifications and/or agents will be apparent to those skilled in the art.

In addition to using antibodies to inhibit or remove stromelysin-3, it may also be possible to use other forms of inhibitor. Such inhibitors may be general (for ECM degrading enzymes, for example), or specific for stromelysin-3. Tissue inhibitors of metalloproteinases (TIMPs) are known to exist, and it is extremely likely that there is a specific TIMP for stromelysin-3. Such a TIMP is easily identifiable by standard techniques.

Synthetic inhibitors of stromelysin-3 may also be manufactured, and these will generally correspond to the area of the substrate affected by the enzymatic activity. It is generally preferred that such inhibitors correspond to a frozen intermediate between the substrate and the cleavage products, but it is also possible to provide a sterically hindered version of the binding site, or a version of the binding site which will, itself, irreversibly bind to stromelysin-3. Other suitable inhibitors will be apparent to the skilled person.

Other methods for blocking stromelysin-3 activity may also be employed. These may constitute denaturing agents, for example, although these tend to be non-specific and could only be adequately employed if they could be targeted, such as by the use of specific antibodies. Other forms of stromelysin-3 blocking activity could be effected by blocking the progress from pre-proprotein through to protein. This process provides several target stages, and it is only necessary to identify a stage which can be independently blocked so as not to affect other vital enzymes, or which can again be targeted.

It may also be possible to use peptides or other small molecules to selectively recognize a tertiary structure on stromelysin-3, thereby blocking its enzymic activity. Such an activity blocker need not necessarily bind the active site, but may serve to alter or freeze the tertiary structure of stromelysin-3, destroying, suspending or altering its activity. The blocker also need not necessarily act by itself, but may be linked to another molecule for this purpose, or may serve as a recognition site for a suitable inactivating agent.

Our studies have demonstrated that the occurrence of type I collagenase and 92 kD type IV collagenase mRNAs is exclusively associated with malignant tumors, although the reverse does not always hold (i.e. tumors are not always associated with these proteins).

There is apparently a parallel between the expression of the stromelysin-3 gene and that of the tenascin gene, in invasive breast carcinomas. The ECM glycoprotein tenascin (Chiquet-Ehrismann et al., Cell 47:131–139 (1986)) appears to play an essential role in epithelial mesenchyme cell interactions and cell migration during normal development, including that of the mammary gland during organogenesis.

Tenascin has consistently been found to be over-expressed in the fibrous stroma of malignant breast tumors, and appears to be induced in a similar manner to stromelysin-3. When compared with fibronectin, tenascin is a poor substrate for attachment of mammary tumor epithelial cells, suggesting that it may allow them to become invasive.

Thus, stromelysin-3 may act in concert with tenascin during the invasive phase of breast cancer. Stromelysin-3 and tenascin may also be co-expressed during embryogenesis in the regions where epithelium-mesenchyme interactions are known to play an important role, and where cell migration is taking place.

Accordingly, the present invention also provides a process for the diagnosis of metastatic cancer as defined above, further comprising the detection of any of the foregoing proteins, or a nucleotide sequence encoding them.

The invention also provides a use in the treatment or prophylaxis of metastic cancer, further comprising the use of an agent to bind any of the foregoing proteins.

The present invention further provides a nucleotide sequence encoding all or part of stromelysin-3. The sequence of stromelysin-3 is preferably that shown in FIG. 2 of the accompanying drawings, whilst the nucleotide sequence is also preferably that shown in FIG. 2. However, it will be appreciated that the nucleotide sequence may be substantially different from that shown in the Figure, due to degeneracy in the genetic code, provided that it still encodes at least a part of stromelysin-3.

The necessary sequence may vary even further, according to the use to which it is to be put. If it is intended for use to detect RNA transcripts in biological samples, then it will usually be preferable that it more nearly corresponds to the sequence given in FIG. 2. However, the sequence may still vary, provided that hydbridization is possible under the selected conditions of stringency.

A probe may be reverse-engineered by one skilled in the art from the peptide sequence of FIG. 2. However use of such probes may be limited, as it will be appreciated that any one given reverse-engineered sequence will not necessarily hybridize well, or at all with any given complementary sequence reverse-engineered from the same peptide, owing to the degeneracy of the genetic code. This is a factor common in the calculations of those skilled in the art, and the degeneracy of any given sequence is frequently so broad as to yield a large number of probes for any one sequence.

If the nucleotide sequence is required for expression of a stromelysin-3 peptide or entire enzyme, then there may be a considerably greater leeway, both as described above with respect to the genetic code, and also to the fact that some amino acid sequence of stromelysin-3 may be varied without significant effect on the structure or function of the enzyme.

If such differences in sequence are contemplated, then it should be borne in mind that there will be critical areas on the molecule which determine activity. Such areas will usually comprise residues which make up the binding site, or which form tertiary structures which affect the binding site. In general, it is possible to replace residues which form the tertiary structure, provided that residues performing a similar function are used. In other instances, the type of residue may be completely unimportant.

Accordingly, the present invention also includes any variants and mutants on the sequence which still show substantial stromelysin-3 activity, or which exhibit characteristic regions of stromelysin-3 for use in generating antibodies, for example. Such variants and mutants include deletions, additions, insertions, inversions, repeats and type-substitutions (for example, substituting one hydrophilic residue for another, but not strongly hydrophilic for strongly hydrophobic as a rule). Small changes will generally have little effect on activity, unless they are an essential part of the molecule, and may be a side-product of genetic manipulation, for example, when generating extra restriction sites, should such be desired. Modification may also include replacement of one or more of the residues with any other suitable residue, and such replacement may either be 1:1 or any other suitable ratio, greater or less than unity.

Spot mutations and other changes in the coding sequence may be effected to add or delete restriction sites, for example, to otherwise assist in genetic manipulation/expression, or to enhance or otherwise conveniently to modify the stromelysin-3 molecule.

It will also be appreciated that a stromelysin-3 equivalent will be found in other animals, especially mammals, and sequence information from such sources can be of particular importance to elucidate the conserved regions of the stromelysin-3 molecule. For example, the corresponding sequence in the mouse is≈80% conserved, including such as the 10 amino acid sequence in the prodomain characteristic of stromelysin-3. It will also be appreciated that animal sequences corresponding to human stromelysin-3 sequences will be readily detectable by methods known in the art and described above, and such sequences and their peptides, as well as mutants and variants thereof, form a part of the invention.

The sequences of the invention may also be engineered to provide restriction sites, if desired. This can be done so as not to interfere with the peptide sequence of the encoded stromelysin-3, or may interfere to any extent desired or necessary, provided that the final product has the properties desired.

As stated above, although hybridization can be an unreliable indication of sequence homology, preferred sequences will generally be those showing in excess of 50%, preferably 70% and more preferably 80% homology with the sequence of FIG. 2.

As with the other metalloproteinases, stromelysin-3 is originally expressed as a pre-proenzyme. Thus, two stages of cleavage are observed in vivo. Cleavage is not necessarily a requirement for in vitro expression, and it may be possible for *E. coli*, for example, to express the mature protein.

Where it is desired to express stromelysin-3 or a characteristic peptide thereof, any suitable system can be used. The general nature of suitable vectors, expression vectors and constructions therefor will be apparent to those skilled in the art.

By "characteristic" is meant any peptide which has a sequence unique to stromelysin-3. Such a sequence may be important to stromelysin-3 activity, or may just be a sequence not found in other peptides. However, sequences important to stromelysin-3 activity are generally preferred, as these are more likely to be conserved within a population.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Again, control sequences, such as recognition, promoter, operator, inducer, terminator and other sequences essential and/or useful in the regulation of expression, will be readily apparent to those skilled in the art, and may be associated with the natural stromelysin-3 sequence or with the vector used, or may be derived from any other source as suitable. The vectors may be modified or engineered in any suitable manner.

Correct preparation of nucleotide sequences may be confirmed, for example, by the method of Sanger et al. (*Proc. Natl. Acad. Sci. USA* 74:5463-7 (1977)).

A cDNA fragment encoding the stromelysin-3 of the invention may easily be inserted into a suitable vector. Ideally, the receiving vector has suitable restriction sites for ease of insertion, but blunt-end ligation, for example, may also be used, although this may lead to uncertainty over reading frame and direction of insertion. In such an instance, it is a matter of course to test transformants for expression, 1 in 6 of which should have the correct reading frame. Suitable vectors may be selected as a matter of course by those skilled in the art according to the expression system desired.

By transforming a suitable organism or, preferably, eukaryotic cell line, such as HeLa, with the plasmid obtained, selecting the transformant with ampicillin or by other suitable means if required, and adding tryptophan or other suitable promoter-inducer (such as indoleacrylic acid) if necessary, the desired stromelysin-3 may be expressed. The extent of expression may be analyzed by SDS polyacrylamide gel electrophoresis—SDS-PAGE (Lemelli, *Nature* 227:680-685 (1970)).

Suitable methods for growing and transforming cultures etc. are usefully illustrated in, for example, Maniatis (*Molecular Cloning, A Laboratory Notebook*, Maniatis et al. (eds.), Cold Spring Harbor Labs, NY (1989)).

Cultures useful for production of stromelysin-3, or a peptide thereof, may suitably be cultures of any living cells, and may vary from prokaryotic expression systems up to eukaryotic expression systems. One preferred prokaryotic system is that of *E. coli*, owing to its ease of manipulation. However, it is also possible to use a higher system, such as a mammalian cell line, for expression of a eukaryotic protein. Currently preferred cell lines for transient expression are the HeLa and Cos cell lines. Other expression systems include the Chinese Hamster Ovary (CHO) cell line.

One valuable system is the baculovirus system, wherein butterfly cells are cotransfected with a DNA vector encoding stromelysin-3, or a suitable peptide, and baculovirus DNA. Recombination occurs within the cell, and suitable baculovirus recombinants may be selected by standard techniques. Thereafter, the recombinant may be used to infect the cell line as desired, stromelysin-3 or peptide being expressed on infection. A particular advantage of this system is the amount of protein produced, which can be in the range of about 1 to about 500 mg/liter.

Although such systems tend not to be as easy to use as the *E. coli* system, the advantage lies in the processing of the protein after primary synthesis. *E. coli*, for example, does not employ the same system for processing pre-proproteins as mammalian cells.

Other expression systems which may be employed include streptomycetes, for example, and yeasts, such as Saccharomyces spp., especially *S. cerevisiae*. Any system may be used as desired, generally depending on what is required by the operator. Suitable systems may also be used to amplify the genetic material, but it is generally convenient to use *E. coli* for this purpose where only proliferation of the DNA is required.

It may be advantageous to produce only the mature enzyme, for the purposes of raising antibodies, as the sequence of the mature enzyme is common to the pro- and prepro sequences also. However, it will be appreciated that cleavage of the pro and prepro portions may alter the tertiary configuration of the molecule, and so it is possible that an antibody raised against the mature enzyme will not detect the proenzyme, for example.

Antibodies raised to the enzyme in either of its earlier states and/or to the pre- or pro-peptides which are cleaved may also prove useful.

The peptide or nucleotide sequence may be any that is characteristic of stromelysin-3, having consideration to the purpose to which it is to be put. Ideally, the sequences would be completely characteristic of stromelysin-3, but the length of such sequences may vary according to the region of the stromelysin-3 molecule. The most preferred regions are those which are highly conserved, and which are not shared with other proteins, although it may be advantageous if the sequence is characteristic of the MMPs or, more particularly, those MMPs associated with invasive tumors.

The invention includes and relates to equivalents of the above peptide and nucleotide sequences, the term "equivalent" being used in the sense of the preceding description, that is to say, equivalents in the sense of sequences having substitutions at the C- or N-terminals, or anywhere else.

The invention also includes mutants of the sequences, the term "mutants" being used with reference to deletions, additions, insertions, inversions and replacement of amino acid residues or bases in the sequence subject to the restrictions described above.

The present invention further includes variants of the sequences, which term is used in relation to other naturally occurring stromelysin-3 which may be discovered from time to time and which shares essentially the same sequence as shown in FIG. 2, but which vary therefrom in a manner to be expected within a large population. Within this definition lie allelic variation and those peptides from other species showing a similar type of activity and having a related sequence. Also included, although less preferred, are animal sequences.

We have also discovered that stromelysin-3 expression can be stimulated by, for example, growth factors and tumor promoters. Typical examples of such factors include EGF FGF and PDGF and TPA. Thus, in conjunction with the foregoing processes, detection of any of these factors in a tumor sample may also help to diagnose the metastatic condition of a cancer.

Thus, the invention also provides the treatment of a metastatic cancer by altering the expression of the stromelysin-3 gene. This may be effected by interfering with the factor required to stimulate stromelysin-3 production, such as by directing specific antibodies against the factor, which antibodies may be further modified to achieve the desired result. It may also be possible to block the receptor for the factor, something which may be more easily achieved by localization of the necessary binding agent, which may be an antibody or synthetic peptide, for example.

Affecting stromelysin-3 gene expression may also be achieved more directly, such as by blocking of a site, such as the promoter, on the genomic DNA.

Where the present invention provides for the administration of, for example, antibodies to a patient, then this may be by any suitable route. If the tumor is still thought to be, or diagnosed as, localized, then an appropriate method of administration may be by injection direct to the site. If the target is breast cancer, then an injection to the breast may suffice, or an implant may be used. If TIMPs are to be administered, for example, then it may also be possible to employ a dermal patch for prolonged administration.

If the cancer is pharyngeal, then a further option may be oral administration, for example, by means of gargling.

In either instance, administration may instead, or additionally, be by injection, including subcutaneous, intramuscular, intravenous and intradermal injections.

Formulations may be any that are appropriate to the route of administration, and will be apparent to those skilled in the art. The formulations may contain a suitable carrier, such as saline, and may also comprise bulking agents, other medicinal preparations, adjuvants and any other suitable pharmaceutical ingredients.

Suitable preparations may also include vaccines comprising stromelysin-3 or a characteristic peptide thereof. Such vaccines may be active or passive, but passive is generally preferred as stromelysin-3 expression occurs in the uterus, and indefinite exposure to antistromelysin-3 antibodies may have undesirable effects. However, active vaccination may be advantageous, especially where a patient has had a hysterectomy, as no tissues will then normally express stromelysin-3. Other suitable vaccines include recombinant viruses containing a nucleotide sequence encoding a stromelysin-3 or a characteristic peptide thereof. One suitable such virus is the vaccinia virus.

The following Examples serve to illustrate the present invention, and are not intended to limit the invention in any manner.

EXAMPLE 1

Cloning of a breast cancer specific cDNA

A breast cancer cDNA library was constructed in the λgt10 vector using poly(A+) RNA from a surgical resection-sample (referred to as tumor C1) of a primary breast cancer. 50,000 plaques were differentially screened using (+) and (−) probes corresponding to cDNAs reverse-transcribed from C1-poly(A+) RNA and poly(A+) RNA from a breast fibroadenoma (referred to as F1), respectively.

Figures 1A, 1B, 1C, 1D:
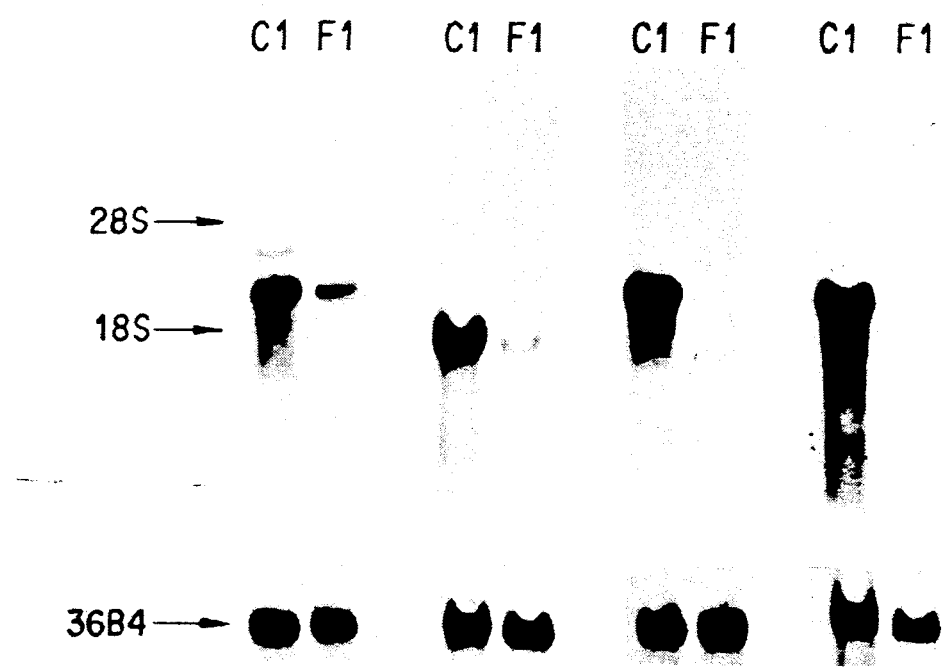
FIG. 1. Northern blot analysis of total RNA from C1 breast carcinoma and Fibroadenoma.

FIG. 1 shows a Northern blot analysis of total RNA from C1-breast carcinoma and F1-fibroadenoma using cDNA probes of four genes (A-D) exhibiting higher levels of expression in the carcinoma than in the fibroadenoma. Each lane contained 8 μg of total RNA. The filters were reprobed using the 36B4 probe which corresponds to an ubiquitously expressed gene (Rio et al., *Proc. Nat. Acad. Sci. USA* 84:9243–9247 (1987)).

Specifically, total RNA was prepared (Chirgwin et al., *Biochemistry* 18:5294–5299 (1979)) from surgical specimens stored in liquid nitrogen, and poly(A+) RNA was selected by oligo(dT)-cellulose chromatography. A breast cancer-enriched cDNA library was constructed using cDNA prepared from an oestrogen receptor-negative, grade II, ductal carcinoma (referred to as C1), in which stromal cells represented approximately 50% of the total cell population.

Prior to cloning, the single-stranded cDNA was substracted with an excess of poly(A+) RNA from a breast fibroadenoma (referred to as F1), and the single-stranded enriched material was purified by hydroxyapatite chromatography (Davis et al., *Proc. Nat. Acad. Sci. USA* 81:2194–2198 (1984); Rhyner et al., *Neuroscience Res.* 16:167–181 (1986)).

The breast cancer-enriched cDNA was made double-stranded and cloned into the EcoRI site of the λgt10 vector. Three million recombinant phages were obtained, and ≈50,000 were differentially screened using replica nylon filters (Biodyne A, Pall Corporation) from plates containing ≈5,000 cDNA clones.

(+) and (−) probes were made using C1-breast cancer cDNA and F1-breast fibroadenoma cDNA, respectively. Both probes were substracted (Davis et al., *Proc. Nat. Acad. Sci. USA* 81:2194–2198 (1984); Rhyner et al., *Neuroscience Res.* 16:167–181 (1986)) with an excess of total human liver RNA before [$^{32}$P]-labeling using random priming synthesis.

Hybridizations were for two days under stringent conditions (50% formamide, 42° C.) and washing was in 2×SSC, 0.1% SDS, at 22° C., followed by 0.1×SSC, 0.1% SDS at 55° C. 130 differentially labelled plaques were selected for a second screening.

The cDNA inserts of five differential plaques taken at random were purified by PCR amplification, [$^{32}$P]-labelled, and hybridized to all of the differential plaques to identify related clones. This procedure was repeated several times with differential plaques taken at random, finally yielding four genes referred to as A to D, which exhibited higher levels of expression in C1-carcinoma than in F1-fibroadenoma. The Northern blots for C1-breast cancer and F1-breast fibroadenoma were prepared using total RNA (8 μg) separated by electrophoresis in 1% agarose gels containing formaldehyde and transferred to Hybond-N filters (Amersham).

The blots were stained with methylene blue before prehybridization to check for the integrity and amounts of transferred RNA. Hybridization (18 h) and washing were performed under standard conditions, as described above, using [$^{32}$P]-labeled cDNA inserts corresponding to A-D genes.

The genes A and B, which were also expressed in normal colon (not shown), were not examined further.

Although expressed in colon (not shown), the C gene was partially characterized because of its high level of differential expression (FIG. 1). It was also expressed in a variety of transformed epithelial cell lines and in normal human skin (not shown). Sequencing of the cDNA of one C clone indicated that the corresponding gene belongs to the keratin gene superfamily (data not shown).

Finally, the D gene (also referred to herein as the stromelysin-3 gene) was further studied, because of its marked differential expression between C1-carcinoma and F1-fibroadenoma (FIG. 1), and also because it was not expressed in normal human colon and in a number of other human tissues (infra).

EXAMPLE 2

Sequencing of Stromelysin-3 Gene and Encoded Protein

Several independent clones were isolated from a non-substracted C1-breast cancer λgt10 cDNA library using a D cDNA insert as probe, and sequenced. FIG. 2 shows the nucleotide sequence of the full length D cDNA and the corresponding protein sequence.

The cDNA open reading frame, encoding a 488 amino acid-long protein, is followed by a 714 base 3′-untranslated region containing a poly(A) addition signal located 14 bases upstream from the 3′-end of the RNA. A presumptive initiation methionine is located at nucleotide position 10–12. Although the corresponding AUG is not associated with and located in a sequence which conforms to the Kozak consensus motif, translation is probably initiated at this AUG, since the sequence immediately downstream corresponds to that for a hydrophobic leader peptide, an expected feature (infra).

In FIG. 2, which shows the nucleotide sequence of stromelysin-3 cDNA and deduced amino acid sequence, the nucleotide residues are numbered in the 5′ to 3′ direction and deduced amino acids in the open reading frame are designated by their one-letter codes. Starting from the 5′-end, the underlined nucleotide sequences correspond to: the putative signal peptide (two potential cleavage sites are marked by arrows); the PRCGVPD sequence characteristic of prometalloproteinases; the conserved histidine residues of the zinc-binding domain (Matrisian, L. M., *Trends Genet.* 6:21–125 (1990)); and the poly(A) addition signal sequence.

Specifically, a cDNA insert corresponding to the 3′-part of D cDNA [250 bp including a 19 bp poly(AT) region] was [$^{32}$P]-labeled by random priming synthesis and used to screen a non-substrated λgt10 cDNA library generated from C1-breast tumor poly(A+) RNA by the method of Gubler and Hoffmann (*Gene* 25:262–269 (1983)]. Several independent clones were identified and subcloned in M13 sequencing vector. DNA sequence was determined by the dideoxy method using sequenase and the deaza-dGTP reagent kit from US Biochemical. The sequence was analyzed using the PC/GENE software package.

EXAMPLE 3

Stomelysin-3, a putative metalloproteinase

FIG. 3 shows a comparison of the predicted amino-acid sequences of human stromelysins and human type I collagenase.

(a) Amino-acid sequences were aligned using a multialignment program (Higgins et al., *Gene* 73:237–244 (1988)). Amino-acid residues identical in all of the four sequences are marked by stars. The arrows denote putative signal peptide eleavage sites of stromelysin-3. The arrowhead points to the cleavage which occurs on activation of type I procollagenase and prostromelysins. The 10 amino-acid residues specific to stromelysin-3 at the level of this cleavage site are boxed. The PRCGVPD sequence and the conserved residues of the putative zincbinding domain are underlined.

(b) Left, regions of similarity (in percent amino-acid identity) between stromelysin-3, stromelysin-1 (ST1, Whitham et al., *Biochem. J.* 240:913–916 (1986)), stromelysin-2 (ST2, Muller et al., *Biochem. J.* 253:187–192 (1988)) and type I collagenase (COI, Whitham et al., *Biochem. J.* 240:913–916 (1986));

(b) Right, regions of similarity between ST1, ST2 and COI; P indicates the signal peptide and the pro-domain; ENZ indicates the domain corresponding to the mature active enzymes.

Thus, comparison of the derived protein sequence with the Swissprot data library (release 14) showed that the new protein belongs to the family of secreted matrix metalloproteinases (MMPs) (FIG. 3a). Accordingly, the new protein possesses an hydrophobic N-terminal leader sequence candidate (underlined in FIG. 2), and exhibits the highly conserved sequence PRCGVPD (amino-acid residues 78–84), which is characteristic of the prodomain of the MMPs, as well as having the zinc binding site of MMPs (amino-acid residues 212–225-FIG. 3a) (Matrisian, L. M., *Trends Genet.* 6:121–125 (1990)).

By analogy with the other members of the family, the N-terminal amino acid of the mature protein is likely to correspond to phenylalanine 98 of the pre-proprotein (Whitham et al., *Biochem. J.* 240:913–916 (1986)) (FIG. 3a). After optimal alignments, the similarity between the putative mature protein is 40% with stromelysin-1 (Whitham et al., *Biochem. J.* 240:913–916 (1986)), 38% with stromelysin-2 (Muller et al., *Biochem. J.* 253:187–192 (1988)) and 36% with type I collagenase (Goldberg et al., *J. Biol. Chem.* 261:6600–6605 (1986)) (FIG. 3b).

The substrate specificity of the new protein is not known. Herein, it is referred to as stromelysin-3, although its similarity with stromelysin-1 (40%) is clearly much below that existing between stromelysin-1 and stromelysin-2 (79%), and even lower than the similarity existing between type I collagenase and stromelysin-1 (53%) (FIG. 3b). Thus, while the protein is an MMP, the cognomen "stromelysin" is not necessarily strictly accurate, but is convenient.

In addition, upstream of the PRCGVPD sequence, there is no significant similarity between stromelysin-3 and the other MMPs with which it is has been compared (FIG. 3). However, stromelysin-3 has a unique short sequence (amino-acid residues 88–97) at a position corresponding substantially precisely with the pro-protein cleavage site of type I collagenase and the stromelysins (Whitham et al., supra). Further, stromelysin-3, as with type I collagenase and the other stromelysins, does not exhibit the fibronectin-like domain characteristic of type IV collagenases (Wilhelm et al., *J. Biol. Chem.* 264:17213–17221 (1989)).

EXAMPLE 4

Over-expression in Breast Carcinomas

The occurrence of stromelysin-3 RNA transcripts was studied in resected samples of 30 breast carcinomas and five breast fibroadenomas.

FIG. 4 shows Northern blot analyses of human metalloproteinase RNAs in breast tumors:
(a) stromelysin-3 RNA;
(b) type I collagenase RNA (COI);
(c) 92-kD type IV collagenase RNA (COIV 92K);
(d) 72-kD type IV collagenase RNA (COIV 72K);
(e) stromelysin-1 and -2 RNA's (ST1/2); and
(f) pump-1 RNA (PUI).

Total RNA was prepared from four oestrogen receptor-negative breast carcinomas (C1, grade II; C2, C3 and C4, grade III), six oestrogen receptor-positive breast carcinomas (C5, C8 and C9, grade II; C6 and C7 grade III; CIO, grade I) and four breast fibroadenomas (F2–F5). Each lane contained 8 μg of RNA. The 36B4 signal corresponds to the RNA of a control gene (FIG. 1).

Specifically, several Northern blots were prepared in parallel with identical RNA samples, as for FIG. 1, and hybridized with either of the following cDNA probes: (a) 1.6 kb insert covering the 3'-part of stromelysin-3 cDNA, (b) COI cDNA, (e) ST2 cDNA (which cross-hybridizes with ST1 RNA), (f) PUI cDNA (COI, ST2 and PU1 probes kindly provided by R. Breathnach, Muller et al., *Biochem. J.* 253:187–192 (1988)), or 80 mer antisense oligonucleotide probes corresponding to (c) COIV 92K (nucleotides 2144–2223, Wilhelm et al., *J. Biol. Chem.* 2641:7213–17221 (1989)) and (d) COIV 72K (nucleotides 1937–2016, Collier et al., *J. Biol. Chem.* 263:6579–6587 (1988)).

The cDNA probes were ($^{32}$P)-labeled using random priming synthesis ($\simeq 5 \times 10^8$ cpm/μg) and the oligonucleotides were labeled using 5'-end kination $\simeq 10_8$ cpm/μg). Hybridizations were carried out under stringent conditions (42° C., 50% formamide) with $\simeq 10^6$ cpm/ml. The filters were then washed in 2×SSC, 0.1% SDS, at 22° C., followed by 0.1×SSC, 0.1% SDS at 55° C. Autoradiography was for (a), 18 h, (b), 20 h, (c), (d) and (e), 4 days, (f), 2 days, at −80° C. with an intensifying screen.

Stromelysin-3 mRNA was found in all of the breast carcinomas, regardless of whether they were oestradiol receptor (ER) positive (C5–C10) or negative (C1–C4) (FIG. 4a), but not in the fibroadenoma samples, with one exception (F2) where the level of expression was similar to the lowest level observed in breast carcinomas.

The occurrence of RNA transcripts of the other members of the MMP gene family was also investigated in the same samples (FIGS. 4b–f). These other members of the MMP family can clearly be separated into two classes, according to their pattern of expression in human breast tumors. The first class includes the 72 kD type IV collagenase (COIV 72K, FIG. 4d), stromelysin-1 and -2 (ST1/2, FIG. 4e) and pump-1 (PU1, FIG. 4f), all of which genes were expressed in both malignant and benign tumors. By contrast, the second class, which includes stromelysin-3 (FIG. 4a), type I collagenase (COI, FIG. 4b) and the 92 kD type IV collagenase (COIV 92K, FIG. 4c) genes, shows over-expression only in breast carcinomas, although only stromelysin-3 was consistently associated therewith.

The patterns of expression were not identical for the three genes of the second class. Type I collagenase RNA transcripts were not detected in the C5, C6, C7 and CIO carcinomas, and the 92 kD type IV collagenase RNA transcripts were not seen in the C7 and CIO samples, but the stromelysin-3 RNA transcripts were clearly detected in all tumors.

Thus, stromelysin-3 appears to be diagnostic of invasive breast carcinomas, while type I collagenase and the 92 kD type IV collagenase may also be specifically involved in breast cancer progression in some cases.

EXAMPLE 5

Expression in Cells from Various Sources

FIG. 5 shows Northern blot analyses of stromelysin-3 RNA in various cell lines and tissues.

(a) Three normal and five metastatic auxillary lymph nodes from patients with breast cancers;

(b) four oestrogen receptor-negative (BT-20, MDA-231, SK-BR3, HBL-100) and four oestrogen receptor-positive (T-47D, BT-474, ZR75-1, MCF-7) breast cancer cell lines;

(c) 10 normal human tissues, (d) HFL-1 human foetal diploid fibroblasts (ATCC CCL 153) cultured in serum-free medium (1 and 2), in the absence (1) or presence (2) of TPA (10 ng/ml) or cultured in serum-free medium supplemented with 20 μg/ml insulin (3 to 6), in the absence (3) or presence (4) of PDGF (20 ng/ml, British Biotechnology), (5) of EGF (20 ng/ml, Collaborative Research) or (6) of bFGF (10 ng/ml, kindly provided by Pettmann (*FEBS Lett.* 189:102–108 (1985))).

In (a), each lane contained 10 μg of total RNA with the exception of lane 5 (2 μg) and lane 6 (20 μg). In (b)

and (c), each lane contained 8 μg of total RNA, and in (d), each line contained 5 μg of cytoplasmic RNA.

Specifically, in (a), (b) and (c) the blots were made and processed as indicated in FIG. 4 for stromelysin-3. In (d), confluent HFL-1 fibroblasts were kept in serum-free DMEM culture medium. After 24 hrs, fresh medium was added and supplemented or not with TPA or growth factors, as indicated above. After 24 hrs of culture, the cells were harvested and cytoplasmic RNA prepared (Gough, N.M., *Analyt. Biochem.* 173:93-95 (1988).

The blots were then prepared and processed as indicated in FIG. 4 for stromelysin-3, but the autoradiography was for three days.

Figure 5A:
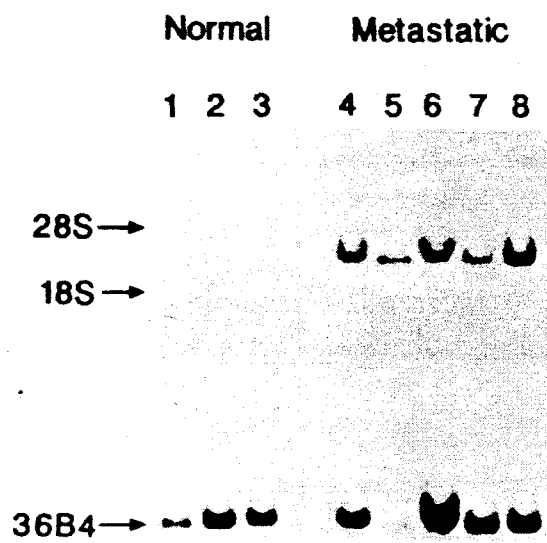

92 kD collagenase IV RNA transcripts were found in 3 normal and 5 breast cancer metastatic lymph nodes, whereas stromelysin-3 RNA transcripts were detected only in the metastatic nodes (FIG. 5a, and data not shown).

Figure 5B:
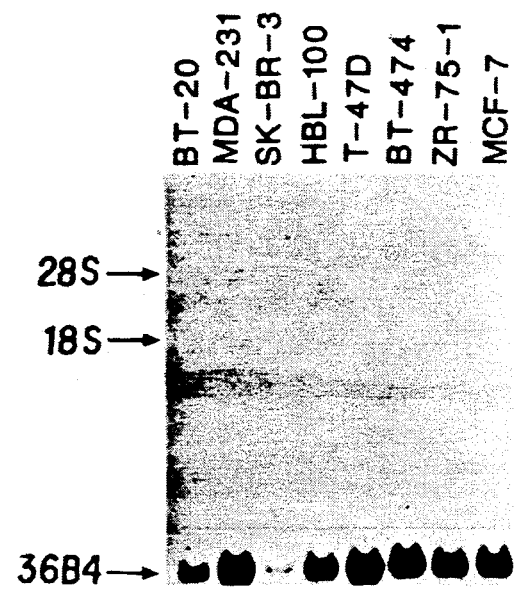
Figure 5C:
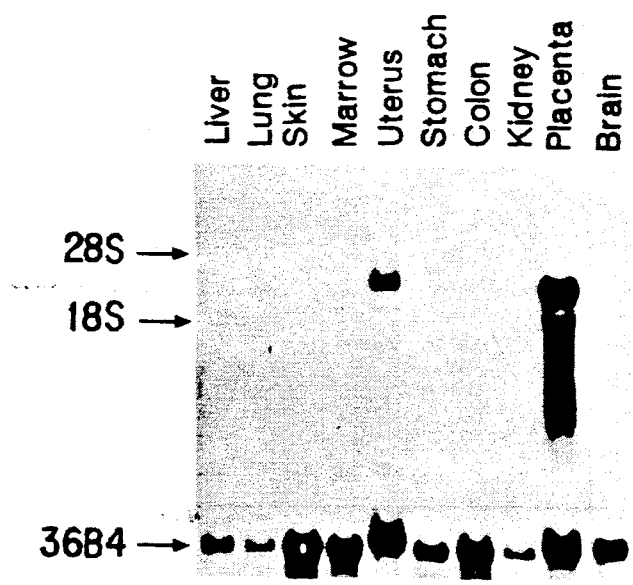

In contrast to the results obtained with primary malignant breast tumors and metastatic lymph nodes, no stromelysin-3 RNA transcripts could be detected under similar conditions in eight human breast cancer cell lines, irrespective of their ER status (FIG. 5b). Similarly, stromelysin-3 RNA transcripts could not be detected in a number of normal human adult tissues (FIG. 5c), with two notable exceptions, uterus and placenta.

Stromelysin-3 is not apparently associated with all cancers, and only low levels of stromelysin-3 RNA transcripts were found in RNA samples from colon, ovary, kidney and lung cancers. However, high levels of expression, comparable to those found in breast cancers, were observed in larynx cancer RNA samples (data not shown).

EXAMPLE 6

Specific Expression in Stromal Cells of Invasive Tumors

The expression of the stromelysin-3 gene in primitive breast carcinomas, but not in a number of established breast cancer cell lines, suggested that the gene was expressed in the stromal cells surrounding the tumor, rather than in the neoplastic cells themselves.

In situ hybridization experiments using a [$^{35}$S]-labelled stromelysin-3 antisense riboprobe were performed using sections from six carcinomas (tumors C1, C3, C5, C9, C10, referred to as for FIG. 4, and tumor C11, an ER-positive carcinoma not shown in FIG. 4).

Specifically, in situ hybridization was carried out as described by Cox et al. (*Dev. Biol.* 101:485-502 (1984)). Deparaffinised and acid-treated sections (6 μm thick) were proteinase K-treated and hybridized overnight with [$^{35}$S]-labelled antisense transcripts from a stromelysin-3 cDNA insert (467 bp extending from nucleotides 1128 to 1594) subcloned in Bluescript II (Stratagene). Hybridization was followed by RNase treatment (20 μg/ml, 30 min, 37° C.) and stringent washing (2×SSC, 50% formamide, 60° C., 2 h), prior to autoradiography using NTB2 emulsion (Kodak). Autoradiography was for 15 days. No significant labeling above background was observed under similar conditions using a sense riboprobe (not shown).

FIG. 6 shows the presence of stromelysin-3 RNA transcripts in sections of breast carcinomas and embryo limb bud. a, c, e, g, i and k: bright fields of tissue sections (×100) stained with haematoxylin; b, d, f, h, j and l: the same sections (still stained with haematoxylin) after in situ hybridization with an antisense stromelysin-3 cRNA probe and dark field imaging.

a and b, grade II ductal breast carcinoma (tumor C1, see FIG. 4): infiltrating cancer cells (C) are surrounded by a stroma rich in fusiform cells (S); stromelysin-3 RNA transcripts are most abundant in the stromal cells immediately surrounding the neoplastic epithelial cells. c and d, grade III ductal breast carcinoma (tumor C3, see FIG. 4): multiple islands of infiltrating breast cancer cells (C) are surrounded by stromal cells; the expression of the stromelysin-3 gene is weaker in the central part of most of the stromal trabeculae (S) i.e. in the region which is the farthest away from the neoplastic cells. e and f: ductal carcinoma, (tumor C3, see FIG. 4) together with two normal lobules (N); stromelysin-3 RNA transcripts were detected exclusively in the stroma apposing the infiltrating cancer cells (C), with the exception of a small area rich in lymphocytes (arrow). g and h, ductal carcinoma (tumor C10, see FIG. 4): stromelysin-3 RNA transcripts can be detected above background in the stromal cells surrounding the infiltrating (upper corner, right) but not the in situ (star) breast cancer cells. i and j, ductal carcinoma (tumor C11, ER-positive, grade II, carcinoma); left: carcinoma in situ (stars), no stromelysin-3 RNA transcripts can be detected in the stromal cells; right: infiltrating neoplastic cells surrounded by stromal cells expressing the stromelysin-3 gene. k and l, interdigital region of an 8-week-old human embryo limb bud: stromelysin-3 RNA transcripts are detected in the mesoderm underlying the primitive epiderm, most notably in the interdigital area (M); note that the primitive epiderm (arrows), the cartilage in formation (PC), and the surrounding mesoderm are not labelled.

In all cases, stromelysin-3 RNA transcripts were detected only in the stromal cells surrounding the islands of malignant epithelial cells which formed the invasive component of the tumors (FIG. 6: panels a and b, for tumor C1; panels c, d, e and f for tumor C3; panels g and h for tumor C10; panels i and j, right hand side, for tumor C11; and data not shown for tumors C5 and C9).

In metastatic lymph nodes (same source as C5) the expression of the stromelysin-3 gene was also restricted to the stromal cells surrounding the metastatic epithelial cells (data not shown).

It is particularly notable that, in all cases, the malignant epithelial cells themselves were not labelled, and that the highest levels of expression were observed in the stromal cells in apposition to the malignant cells. In marked contrast, no significant expression could be detected in the stromal cells surrounding in situ carcinoma lesions still surrounded by a basement membrane (panels g and h for tumor C10; panels i and j, left hand side, for tumor G11), while the labelling of stromal cells could be clearly observed in the invasive component of the same tumors (panels g and h for tumor CIO; panels i and j, right hand side, for tumor C11).

Figure 4A:
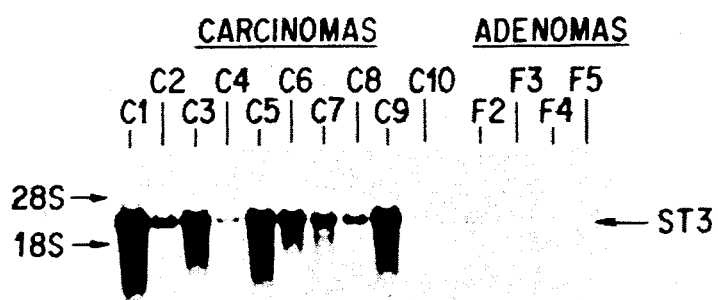
Figure 4B:
Figure 4C:
Figure 4D:
Figure 4E:
Figure 4F:
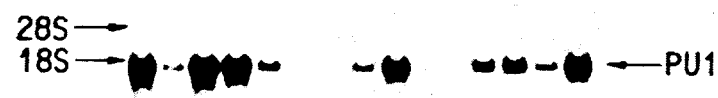

Also, no significant expression could be detected in stromal cells located at a distance from the cancerous cells nor in the stromal cells surrounding normal ducts and ductules (e.g. panels e and f). No discrete foci of stromelysin-3 transcripts were detected in sections of the F2 fibroadenoma weakly positive for stromelysin-3 RNA on Northern blots (FIG. 4a and not shown).

Both fibroblasts and myofibroblasts are known to be present in the stroma of invasive breast carcinomas (Ahmed, A., *Pathol. Annu.* 25(Pt2):237-286 (1990)).

Using our in situ hybridization technique, it was not possible to determine whether only one or both of these cell types expressed stromelysin-3 gene.

EXAMPLE 7

Stimulation by Growth Factors

The above results indicate that expression of the stromelysin-3 gene in stromal cells is likely to be induced by a diffusible factor secreted by the neoplastic cells. Growth factors such as EGF, FGF and PDGF, as well as some cytokines (IL-1α,β, and TNF-α), and tumor promoters (e.g. TPA) are known to activate the transcription of MMP genes (Kerr et al., *Science* 242:1424–1427 (1988)). It has been also reported that tumor cells from several sources produce a factor(s) which stimulates collagenase I production by human fibroblasts (Lippman et al., *Recent Prog. Hormone Res.* 45:383–440 (1990)). PDGF, FGF and TGF-α activities are known to be secreted by breast cancer cells in vitro (Salomon et al., in *Breast cancer: cellular and molecular biology* (eds., Lippman, M. E. and Dickson, R. B.), pp. 363–389 (Kluwer, Boston, (1988)).

Figure 5D:
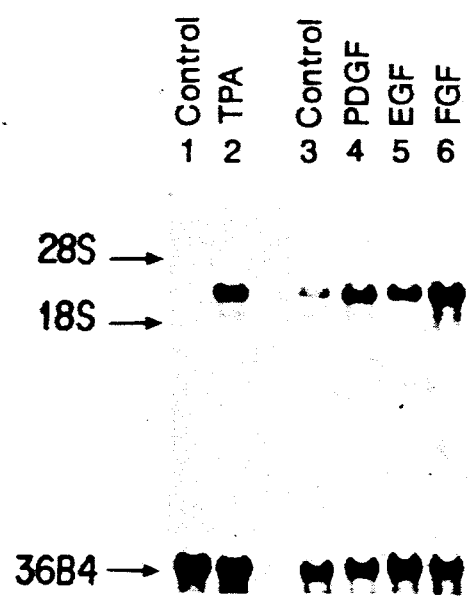
Figure 6A:
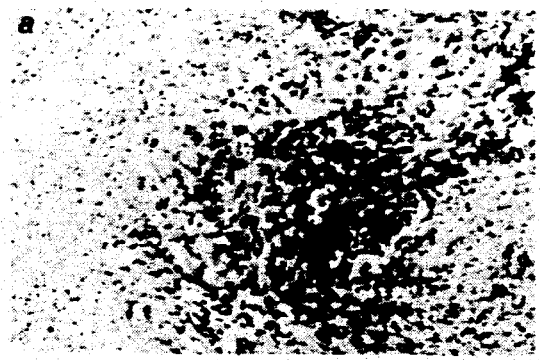
Figure 6B:
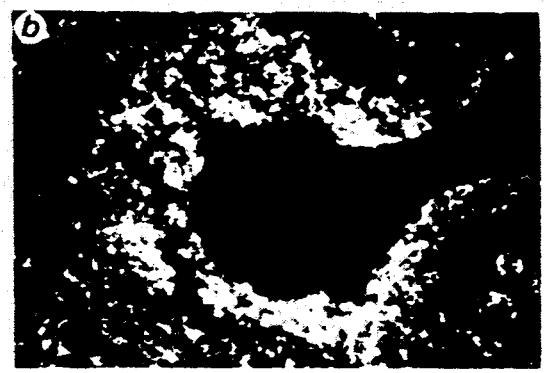
Figure 6C:
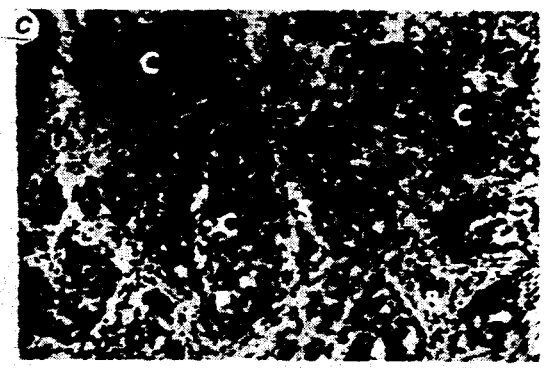
Figure 6D:
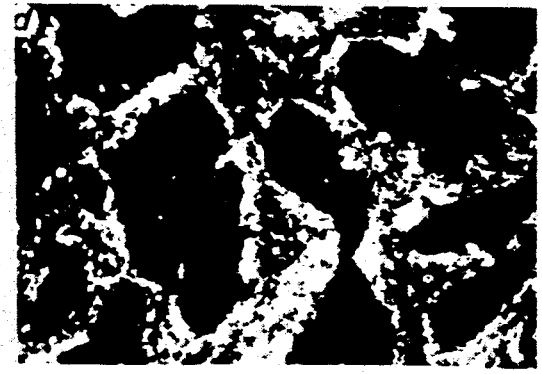
Figure 6E:
Figure 6F:
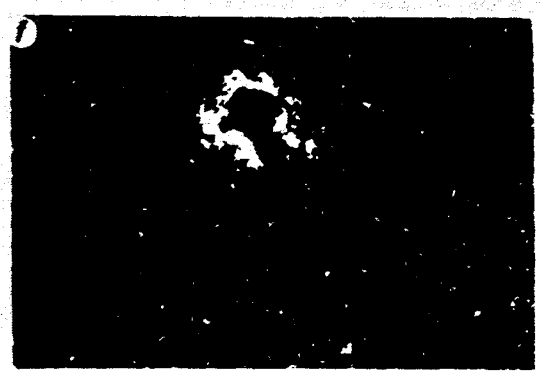
Figure 6G:
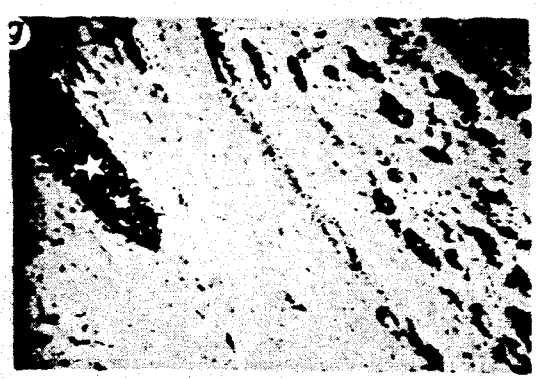
Figure 6H:
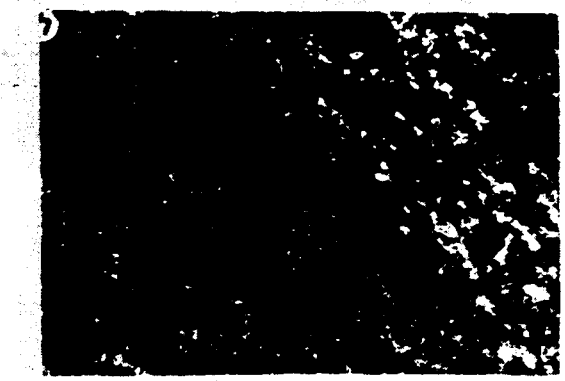
Figure 6I:
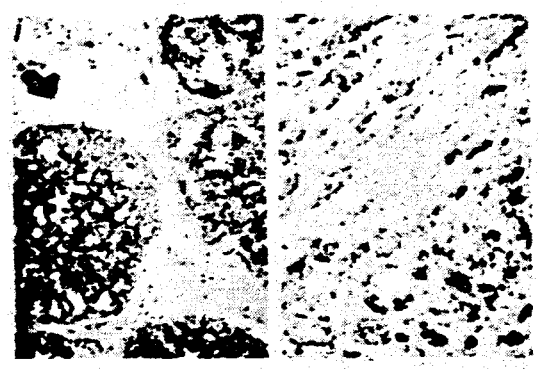
Figure 6J:
Figure 6K:
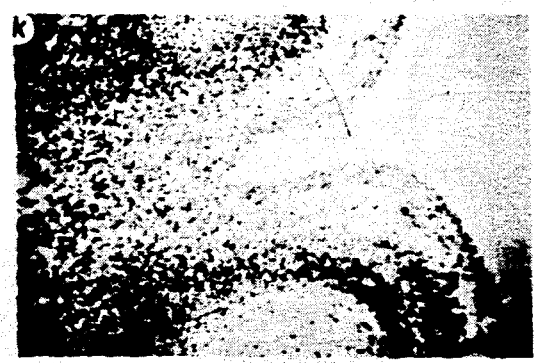
Figure 6L:

To investigate whether stromelysin-3 gene expression could be modulated by exogenous stimuli, human foetal diploid fibroblasts were grown in the absence or presence of either PDGF, bFGF and EGF, and also of the tumor promoter TPA. Addition of either of these growth factors or of TPA resulted in an increase of stromelysin-3 RNA transcripts in the fibroblasts, the strongest stimulation being observed with bFGF (FIG. 5d).

EXAMPLE 8

Stromelysin-3 Expression in the Embryo

As the stromelysin-3 gene was expressed in response to stimulation by growth factors in foetal fibroblasts, we investigated whether the gene might be normally expressed during embryo development.

Stromelysin-3 transcripts were detected in several discrete regions of an 8-week-old human embryo, notably in the interdigital region of the limb buds (FIG. 6, panels k and l, and data not shown), an area known to be associated with programmed cell death at this stage of embryogenesis (Milaire, J., *Organogenesis* (eds., De Haan, R. L. and Ursprung, H.), pp. 283–300 (Holt, Rinehart and Winston, N.Y., 1965)).

The labelling was observed in the embryonic mesoderm underlying the primitive epiderm which remained unlabelled. Notably, the mesenchymal cells located at a distance from the epiblast were also mRNA-negative.

Thus, the finding that the stromelysin-3 gene is expressed during normal embryonic development in an area where tissue remodelling is well documented suggests that expression of stromelysin-3 in breast tumors plays a role in the ECM remodelling processes associated with cancer progression.

EXAMPLE 9

Cloning of mouse cDNA encoding ST3

A probe containing human cDNA encoding ST3 was used to screen a mouse placental cDNA library using standard procedures (Sambrook et al., *Molecular Cloning: A Laboratory Manual*, Cold Spring Harbor Press (1989)). The screening resulted in obtaining a full length mouse cDNA encoding ST3 (FIG. 7).

An analysis of the two sequences revealed a 89% homology in the amino acid sequence of the mature form of ST3 and approximately a 55% homology at the pre and prodomains (FIG. 7).

The pattern of expression in various mouse cells was determined using the methods described in Examples 4–8.

The pattern of ST3 expression in mouse was found to be identical with respect to tissue specificity as that found with human tissue. The highest level of expression was found in placental and uteran tissue.

---

We claim:

1. A cDNA encoding either mouse (SEQ. ID No. 3) or human (SEQ. ID No. 1) stromelysin-3, or fragment thereof.

2. The vector of claim 1 wherein said vector directs the expression of said cDNA.

3. The cDNA of claim 1 wherein said cDNA is contained in a vector.

4. The vector of claims 3 or 2 wherein said vector is selected from the group consisting of plasmid, phage, cosmid, retrovirus and baculovirus.

5. The cDNA of claim 1 wherein said cDNA encodes human stromelysin-3.

6. The cDNA of claim 5 wherein said cDNA is depicted in Sequence ID No. 1.

7. The cDNA of claim 1 wherein said cDNA encodes mouse stromelysin-3.

8. The cDNA of claim 7 wherein said cDNA is depicted in Sequence ID No. 3.